US009916435B2

United States Patent
Fram

(10) Patent No.: US 9,916,435 B2
(45) Date of Patent: *Mar. 13, 2018

(54) SYSTEM AND METHOD FOR THE DISPLAY OF RESTRICTED INFORMATION ON PRIVATE DISPLAYS

(71) Applicant: D.R. Systems, Inc., San Diego, CA (US)

(72) Inventor: Evan K. Fram, Paradise Valley, AZ (US)

(73) Assignee: D.R. Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/356,082

(22) Filed: Nov. 18, 2016

(65) Prior Publication Data

US 2017/0068813 A1 Mar. 9, 2017

Related U.S. Application Data

(63) Continuation of application No. 14/509,721, filed on Oct. 8, 2014, now Pat. No. 9,536,106.

(60) Provisional application No. 61/888,757, filed on Oct. 9, 2013, provisional application No. 61/888,372, filed on Oct. 8, 2013.

(51) Int. Cl.
*H04L 29/06* (2006.01)
*G06F 17/30* (2006.01)
*G06F 21/44* (2013.01)
*G06F 21/62* (2013.01)
(Continued)

(52) U.S. Cl.
CPC ........ *G06F 21/44* (2013.01); *G06F 17/30861* (2013.01); *G06F 19/321* (2013.01); *G06F 19/322* (2013.01); *G06F 19/3406* (2013.01); *G06F 21/6245* (2013.01); *H04L 63/102* (2013.01); *H04L 63/105* (2013.01); *G06F 2221/032* (2013.01)

(58) Field of Classification Search
None
See application file for complete search history.

(56) References Cited

U.S. PATENT DOCUMENTS

| 6,151,023 | A | * | 11/2000 | Chari | .................... G06F 9/4411 |
| | | | | | 709/223 |
| 8,606,656 | B1 | * | 12/2013 | Franklin | ................ G06Q 30/06 |
| | | | | | 705/27.1 |
| 8,954,884 | B1 | | 2/2015 | Barger | |
| 9,536,106 | B2 | | 1/2017 | Fram | |
| 2002/0147717 | A1 | | 10/2002 | Barros | |
| 2003/0055686 | A1 | | 3/2003 | Satoh | |
| 2003/0184585 | A1 | | 10/2003 | Lin et al. | |
| 2005/0114788 | A1 | | 5/2005 | Fabritius | |

(Continued)

OTHER PUBLICATIONS

U.S. Appl. No. 14/593,330, filed Jan. 9, 2015, Systems and User Interfaces for Dynamic Interaction With Two- and Three-Dimensional Medical Image Data Using Spatial Positioning of Mobile Devices.

(Continued)

*Primary Examiner* — Eric Chen
(74) *Attorney, Agent, or Firm* — Knobbe, Martens, Olson & Bear, LLP

(57) ABSTRACT

The present invention is directed to a system and method for restricting data, or portions thereof, to specific display devices when accessed by a user. Furthermore, the system and method of the invention are directed, in part, to evaluating in real time, the access level of a device and restricting the availability of sensitive information on the device according to the access level as determined by device location and hardware configuration.

20 Claims, 14 Drawing Sheets

(51) Int. Cl.
  *G06F 19/00* (2018.01)
  *G06F 7/04* (2006.01)

(56) References Cited

U.S. PATENT DOCUMENTS

| | | | | |
|---|---|---|---|---|
| 2005/0228874 | A1* | 10/2005 | Edgett | H04L 63/08 709/220 |
| 2006/0017692 | A1 | 1/2006 | Wehrenberg | |
| 2006/0223556 | A1 | 10/2006 | Xu | |
| 2006/0236373 | A1 | 10/2006 | Graves et al. | |
| 2006/0288095 | A1 | 12/2006 | Torok et al. | |
| 2007/0006289 | A1* | 1/2007 | Limont | H04W 8/22 726/6 |
| 2007/0143851 | A1* | 6/2007 | Nicodemus | G06F 21/55 726/25 |
| 2007/0282631 | A1 | 12/2007 | D'Ambrosia | |
| 2008/0094368 | A1 | 4/2008 | Ording | |
| 2009/0138800 | A1 | 5/2009 | Anderson | |
| 2009/0222914 | A1* | 9/2009 | Ozawa | G06F 21/608 726/21 |
| 2010/0017874 | A1* | 1/2010 | Piccinini | G06F 21/71 726/18 |
| 2010/0131294 | A1 | 5/2010 | Venon | |
| 2010/0199197 | A1* | 8/2010 | Faletski | G06F 17/30905 715/760 |
| 2010/0240996 | A1 | 9/2010 | Ionasec et al. | |
| 2010/0271177 | A1 | 10/2010 | Pang | |
| 2010/0313239 | A1* | 12/2010 | Chakra | G06F 21/6218 726/2 |
| 2011/0122155 | A1* | 5/2011 | Zechlin | G06F 17/30905 345/660 |
| 2012/0133601 | A1 | 5/2012 | Marshall | |
| 2012/0154431 | A1 | 6/2012 | Fram | |
| 2012/0183173 | A1* | 7/2012 | Li | G06K 9/00744 382/100 |
| 2012/0190301 | A1 | 7/2012 | Hart | |
| 2012/0233670 | A1* | 9/2012 | Bonnes | G06F 21/604 726/4 |
| 2012/0239950 | A1* | 9/2012 | Davis | H04W 12/06 713/320 |
| 2012/0253845 | A1 | 10/2012 | Bocirnea | |
| 2012/0254981 | A1* | 10/2012 | Levien | G06F 21/35 726/16 |
| 2012/0297490 | A1* | 11/2012 | Barraclough | G06F 21/10 726/26 |
| 2012/0323607 | A1 | 12/2012 | Jin et al. | |
| 2013/0141366 | A1 | 6/2013 | Ritter | |
| 2013/0218583 | A1 | 8/2013 | Marcolongo et al. | |
| 2013/0218917 | A1 | 8/2013 | Bell | |
| 2013/0253291 | A1 | 9/2013 | Dixon et al. | |
| 2013/0316682 | A1* | 11/2013 | Vieira | H04W 12/08 455/414.1 |
| 2013/0347055 | A1* | 12/2013 | Motoyama | G06F 21/00 726/1 |
| 2014/0075502 | A1* | 3/2014 | Aissi | G06F 21/60 726/1 |
| 2014/0078694 | A1 | 3/2014 | Wissmar | |
| 2014/0100955 | A1 | 4/2014 | Osotio | |
| 2014/0135036 | A1 | 5/2014 | Bonanni | |
| 2014/0282943 | A1* | 9/2014 | Nikankin | H04L 63/0884 726/6 |
| 2014/0324469 | A1 | 10/2014 | Reiner | |
| 2014/0343962 | A1* | 11/2014 | Xu | G06F 19/322 705/3 |
| 2015/0101066 | A1 | 4/2015 | Fram | |

OTHER PUBLICATIONS

U.S. Appl. No. 14/593,228, filed Jan. 9, 2015, Systems and User Interfaces for Dynamic Interaction With and Detection of Relevant Medical Patient Information Based on Patient Proximity.

Agfa HealthCare, color brochure "IMPAX 6: Digital Image and Information Management," © 2012 Agfa HealthCare N.V. Downloaded from http://www.agfahealthcare.com/global/en/he/library/libraryopen?ID=32882925. Accessed on Feb. 9, 2015.

Agfa HealthCare, IMPAX 6.5 Datasheet (US)2012. © 2012 Agfa HealthCare N.V. Downloaded from http://www.agfahealthcare.com/global/en/he/library/libraryopen?ID=37459801. Accessed on Feb. 9, 2015.

AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.

ASPYRA's Imaging Solutions, 3 page color print out. Accessed at http://www.aspyra.com/imaging-solutions. Accessed on Feb. 9, 2015.

Avreo, interWorks—RIS/PACS package, 2 page color brochure, © 2014, Avreo, Inc. (Document MR-5032 Rev. 4). Downloaded from http://www.avreo.com/ProductBrochures/MR-5032Rev.%204 interWORKS%20RISPACSPackage.pdf. Accessed on Feb. 9, 2015.

BRIT Systems, BRIT PACS View Viewer, 2 page color brochure, (BPB-BPV-0001). Downloaded from http://www.brit.com/pdfs/britpacsview.pdf. Accessed on Feb. 9, 2015.

BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.

BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.

CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.

Carestream, Cardiology PACS, 8 page color brochure. (CAT 866 6075 Jun. 2012). © Carestream Health, Inc., 2012. Downloaded from http://www.carestream.com/cardioPACS_brochure_M1-877.pdf. Accessed on Feb. 9, 2015.

Carestream, Vue PACS, 8 page color brochure. (CAT 300 1035 May 2014). © Carestream Health, Inc., 2014. Downloaded from http://www.carestream.com/csPACS_brochure_M1-876.pdf. Accessed on Feb. 9, 2015.

Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.

CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.

DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.

DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.

Fujifilm Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.

Fujifilm Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.

Fujifilm Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.

(56) References Cited

OTHER PUBLICATIONS

GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Features of Handy Patients Enterprise, in 4 page printout. Accessed from http://www.handylife.com/en/software/features.html. Accessed on Feb. 18, 2015.
Handylife.com—Overview of Handy Patients Enterprise, in 2 page printout. Accessed from http://www.handylife.com/en/software/overview.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See The Future, in 12 pages, color brochure, (BRO80809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page on color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.

NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer Pacs, Lite PACS, XU PACS Compare RamSoft PACS Products, 2 color page printout. Accessed at http://www.ramsoft.com/products/powerserver-pacs-overview. Accessed on Feb. 9, 2015.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
ScImage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 1/07). © 2007 Stryker. Downloaded from http://www.stryker.com/emea/Solutions/Imaging/OfficePACSPowerDigitalImaging/ssLINk/emea/1557/02268. Accessed on Feb. 9, 2015.
UltraRAD—ultra VISION, 1 page (color). Downloaded from http://www.ultraradcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager Pacs, 3 page color brochure. Downloaded from http://www.intellirad.com.au/index.php/assets/Uploads/Voyager-Pacs3.pdf. Accessed on Feb. 9, 2015.
Restriction Requirement dated Oct. 31, 2016 in U.S. Appl. No. 14/593,330.
Office Action dated Dec. 16, 2016 in U.S. Appl. No. 14/593,330.
Interview Summary dated Feb. 9, 2017 in U.S. Appl. No. 14/593,330.
Final Office Action dated Jun. 2, 2017 in U.S. Appl. No. 14/593,330.

(56) References Cited

OTHER PUBLICATIONS

Interview Summary dated Aug. 3, 2017 in U.S. Appl. No. 14/593,330.
Office Action dated Oct. 5, 2017 in U.S. Appl. No. 14/593,330.
Office Action dated Oct. 16, 2017 in U.S. Appl. No. 14/593,228.
Office Action dated Feb. 16, 2016 in U.S. Appl. No. 14/509,721.
Interview Summary dated Apr. 26, 2016 in U.S. Appl. No. 14/509,721.
Final Office Action dated Jun. 21, 2016 in U.S. Appl. No. 14/509,721.
Final Office Action dated Aug. 2, 2016 in U.S. Appl. No. 14/509,721.
Notice of Allowance dated Sep. 27, 2016 in U.S. Appl. No. 14/509,721.

* cited by examiner

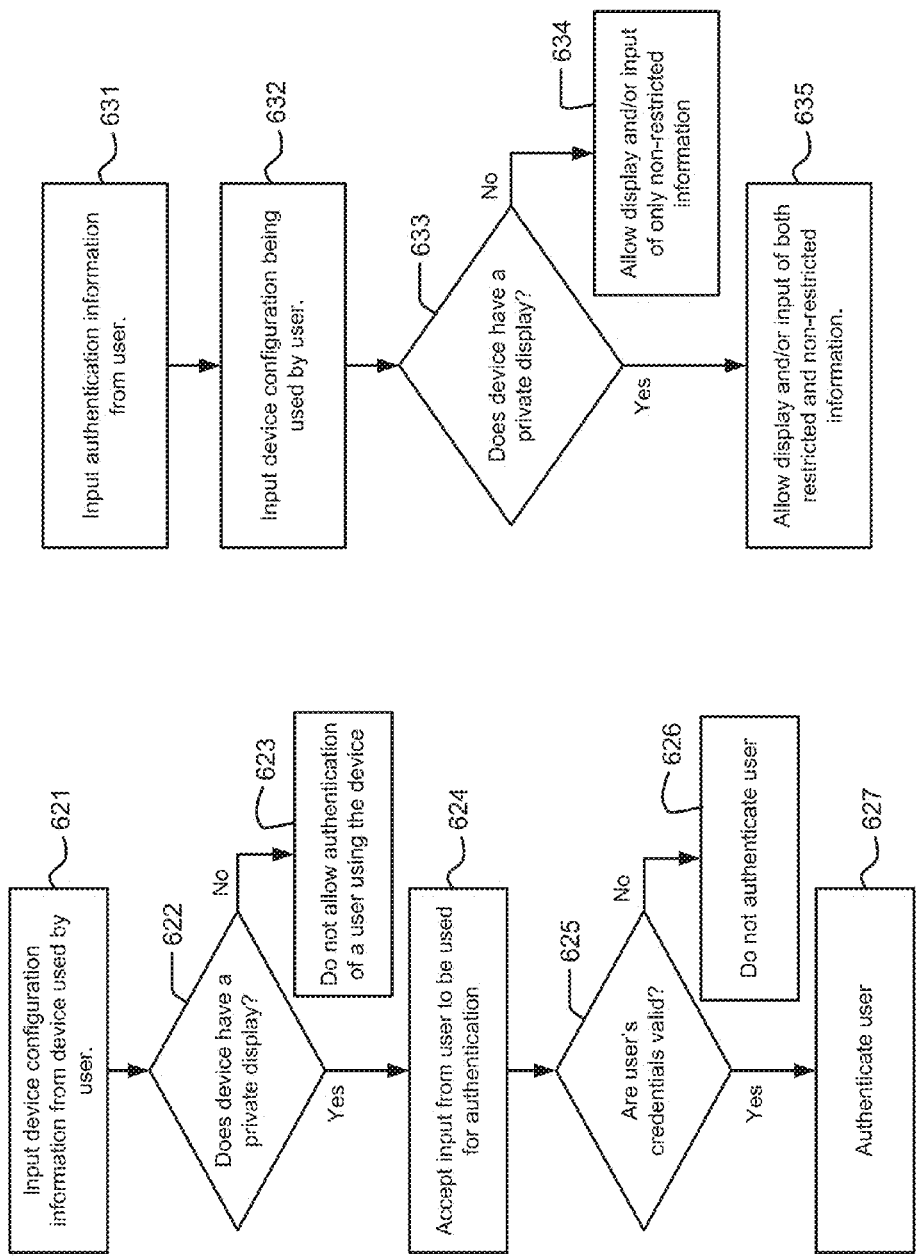

SYSTEM AND METHOD FOR THE DISPLAY OF RESTRICTED INFORMATION ON PRIVATE DISPLAYS

CROSS-REFERENCE TO RELATED APPLICATIONS

This application is a continuation of U.S. patent application Ser. No. 14/509,721, filed Oct. 8, 2014, which application claims benefit of U.S. Provisional Patent Application No. 61/888,757, filed Oct. 9, 2013 and U.S. Provisional Patent Application No. 61/888,372, filed Oct. 8, 2013. The entire disclosure of each of the above item is hereby made part of this specification as if set forth fully herein and incorporated by reference for all purposes, for all that it contains.

Any and all applications for which a foreign or domestic priority claim is identified in the Application Data Sheet as filed with the present application are hereby incorporated by reference under 37 CFR 1.57.

FIELD OF THE INVENTION

The present invention is directed to a system and method for restricting data, or portions thereof, to specific display devices when accessed by a user. Furthermore, the system and method of the invention are directed, in part, to evaluating in real time, the access level of a device and restricting the availability of sensitive information on the device according to the access level.

BACKGROUND OF THE INVENTION

In many environments where people use computers, their computer display may be visible to other users. This can be a significant problem when the displayed information is private, restricted, or sensitive.

For example, doctors and other healthcare workers routinely display patients' private healthcare information on computer monitors in hospitals, clinics, and doctors' offices. With the migration of medical records to digital form, including the use of Electronic Medical Records systems (EMR), this practice is only set to increase.

A doctor using a computer to view his patient's healthcare information at a nursing station may be authorized to view that information. However, other doctors and healthcare workers at the nursing station, unassociated with the patient, may not be authorized to view that same private information, or some portions of the patent's information. Laws such as HIPAA require that the privacy of healthcare information be protected, and significant penalties can be incurred for failing to do so.

Therefore, a problem arises of restricting data to only authorized users, when such data is only obtainable or useful in a public, or semi-private setting. This problem extends beyond the medical field to other situations in which private, restricted, or sensitive information may be viewed on computers. For example, financial, or other confidential information might be displayed at inopportune times and locations in an office, showroom or factory.

SUMMARY OF THE INVENTION

In one arrangement of a system and method described herein, a computer system is configured to selectively display, or to transmit for display, data depending on the accessibility level of the requesting device. In one particular configuration, the present invention is directed to a computer implemented method for selectively displaying information stored in a server or database on a remote display device, the method comprising, using a remote display device to request, using a data request module, a dataset stored in the memory of a remote computer, the dataset having a specified access restriction level; transmitting, to a computer controlling access to the dataset having a specified access restriction level, at least data relating to the display characteristics of the remote display device using a device configuration module which comprises code executing in a processor. The method also includes identifying the access restriction level of the display device using a restriction level module which comprises code executing in the processor; and comparing, with a comparison module configured as code executing in the processor, the access restriction level of the display device and the access restriction level of the requested dataset. Furthermore, once the access level of the requesting device has been compared to the access level of the requested data, the processor is configured to transmit the requested dataset to the display device when (i.e., upon determination that) the access restriction level of the display device is above a pre-set threshold using a transmission module. The display device is then caused to display the dataset with a display module configured as code executing in a processor.

In a further, optional arrangement, in addition to conditioning the transmission of the requested dataset upon the access restriction level being determined as being above a pre-set threshold, the transmission can be further conditioned to be based upon a determination of the device type and or ID of the device to which the dataset is to be transmitted for an assessment as to whether to complete that task, and arranged to not transmit the requested dataset in the event that the transmission is being directed to hardware fails the assessment. As such, requested datasets can be controllably distributed in response to requests only to approved or known displays, mobile devices, and so on.

The system and method, in more particular arrangements in accordance with certain implementations of the invention, can also include the use of a location awareness module, configured as code executed on a processor, which cause the processor to evaluate the access condition level of the features of the data object and determines based on location, to display or restrict the information.

The system and method described further includes providing a user with options for displaying sensitive or private information across a combination of conventional computer displays, specialized computer displays, and mobile devices that have screens that are easily viewed by the user but not by others. This combination allows a user to efficiently interact with a computer with a standard computer monitor, but only view restricted information using devices that have "private displays," i.e. displays that are easily viewed by the user but not others nearby.

These and other aspects, features, and arrangements of the invention can be appreciated from the accompanying drawing figures and discussion of certain embodiments of the invention.

BRIEF DESCRIPTIONS OF THE DRAWINGS

FIGS. 6A-6D provides examples of the steps taken by an information restriction system in accordance with embodiments described herein.

Figure 7:
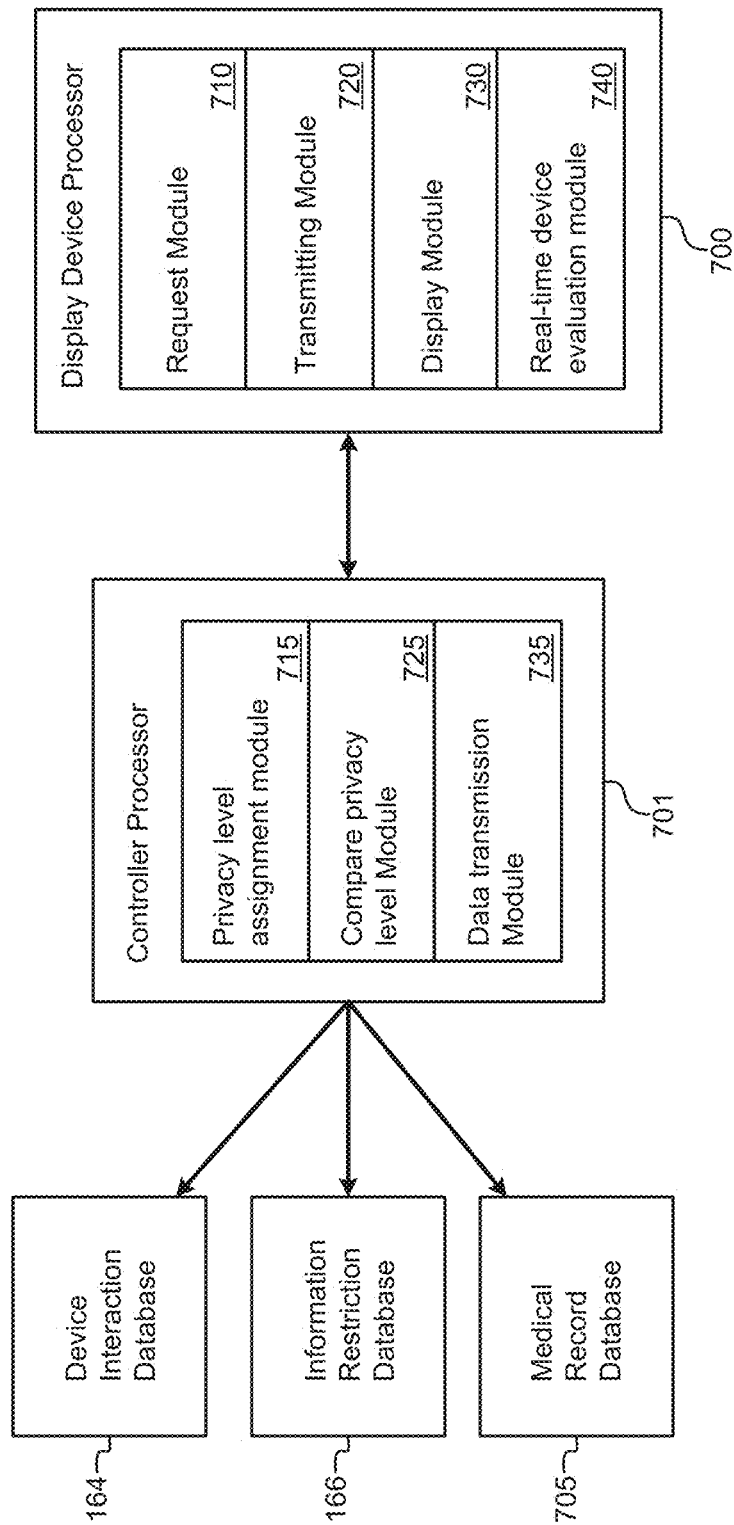

FIG. 7 provides a block diagram of an example system in accordance with an embodiment of the present invention.

Figure 8:
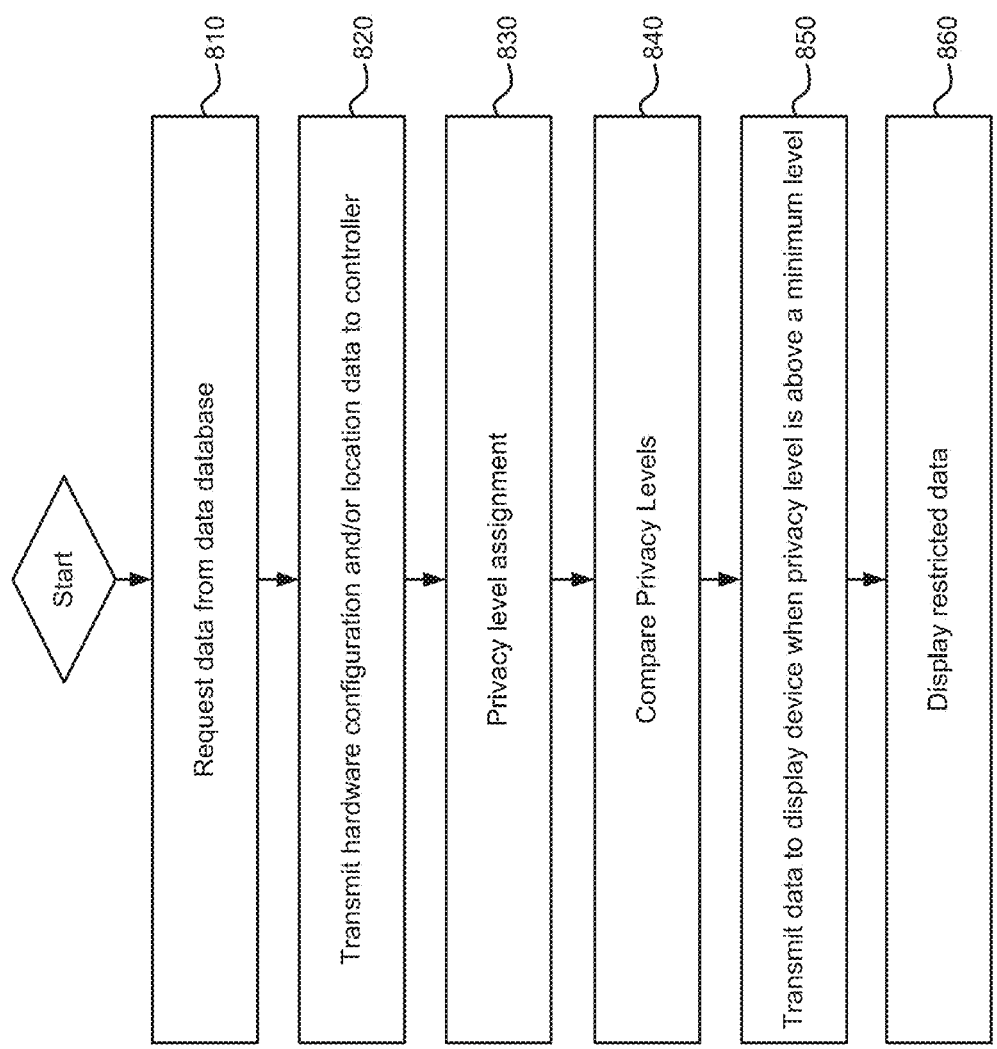

FIG. 8 provides a flow detailing the steps of an embodiment of the method described herein.

Figure 9:
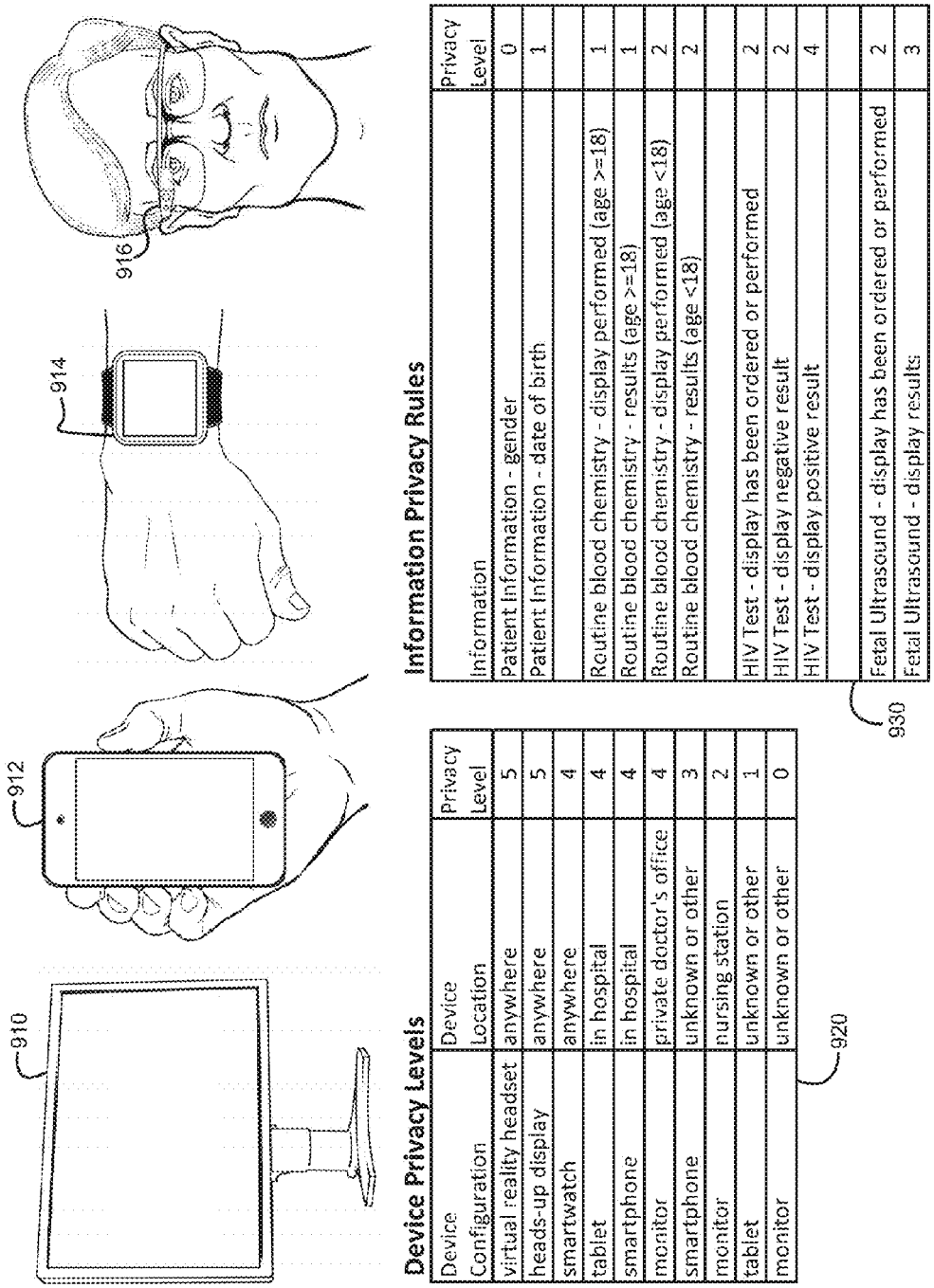

FIG. 9 provides examples of displays with various restriction levels and examples of device privacy levels and information privacy rules according to an embodiment of the present invention.

Figure 10:
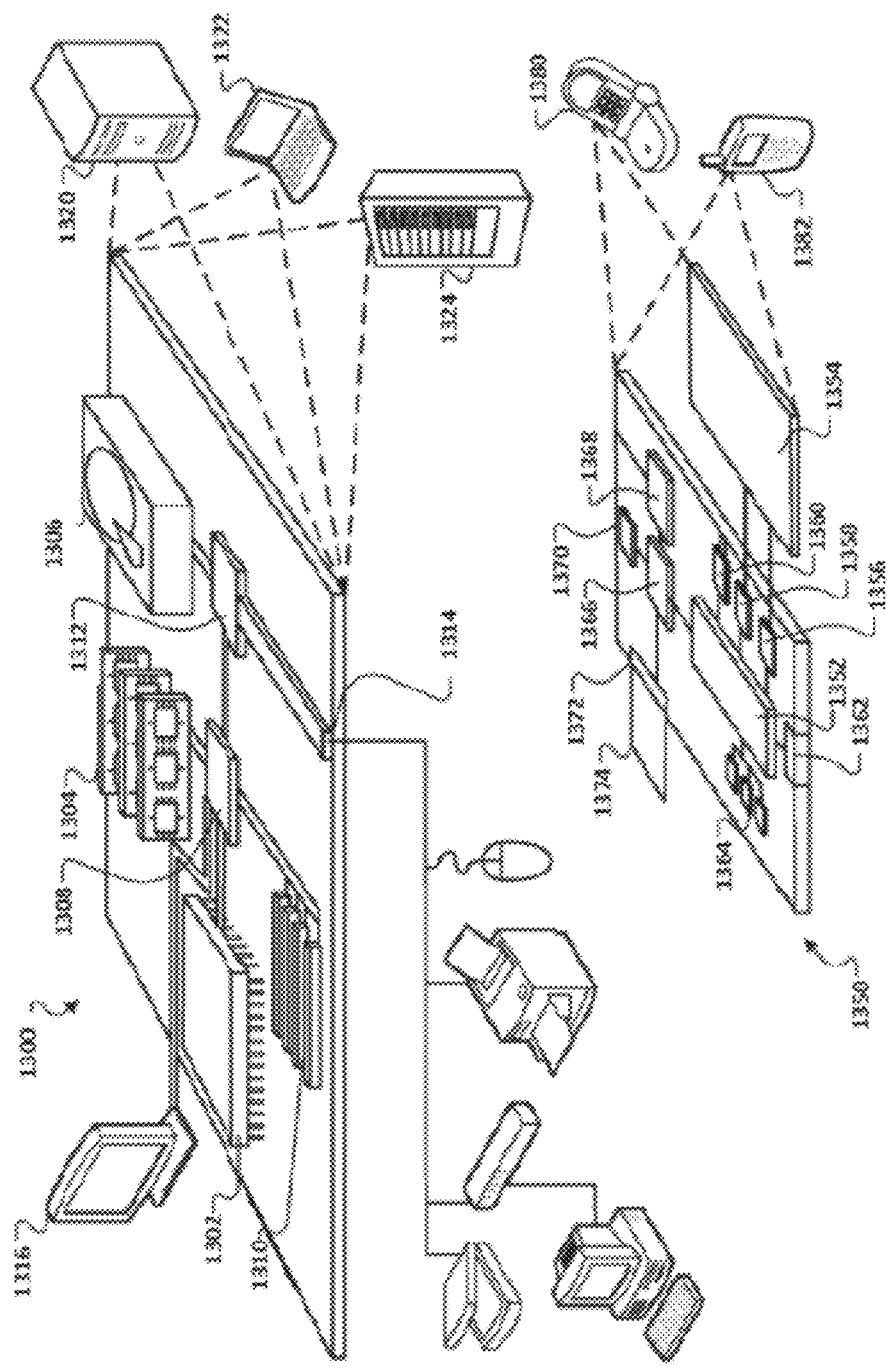

FIG. 10 is an illustrated diagram of the elements of the system of an embodiment of the present invention.

DETAILED DESCRIPTION OF CERTAIN EMBODIMENTS OF THE INVENTION

By way of overview and introduction, the system and methods describe a computer system configured to restrict access and distribute private information to approved access devices depending on a privacy level associated with that device.

As used herein, and for the purposes of discussion, information that a user deems to be particularly private, restricted or sensitive, will be termed "restricted" or "private." For example, private or restricted information is data or information which a user prefers, or is obligated, legally or contractually, to keep confidential or not to disclose to a third party without consent. As will be appreciated from context, the verb "restricting" refers to the actions taken in response to instructions executing in a processor to control information flow such as to a particular display.

Furthermore, the "privacy level" of a device is determined according to a combination of factors, including but not limited to, the type of private information the user seeks to display, the location of the user, and the nature of the display device that the user is attempting the access and display the information.

For ease of explanation, the following examples refer to medical records. However, those possessing a level of ordinary skill in the art will appreciate that additional private material, such as government documents, financial records, personal communications, and commercial or journalistic materials are envisioned and contemplated by the described system and method.

Likewise, as used herein, "data" can be any information conveyable to a user through a device. For example data can include audio data, audiovisual data, images, 3D renderings or simulations, as well as web links or system portals to remotely accessible software or datasets. Purely for illustration purposes, and as a non-limiting example, the data could incorporate multiple types of data, such as both an audio file and a 3D image associated with it.

Furthermore, the terms "viewer" and "user" are used interchangeably to describe an individual (or group of individuals) that interfaces with a computing device of the present invention. As another non-limited example, users or viewers can include medical professionals such as radiologists and other doctors, as well as hospital staff, or other individuals involved in acquisition, interpretation, analysis, storage, management, or other tasks related to medical images. In other embodiments, users can include any individuals or groups of individuals that generate, transmit, view, and/or otherwise work with images of any type.

Figure 1A:
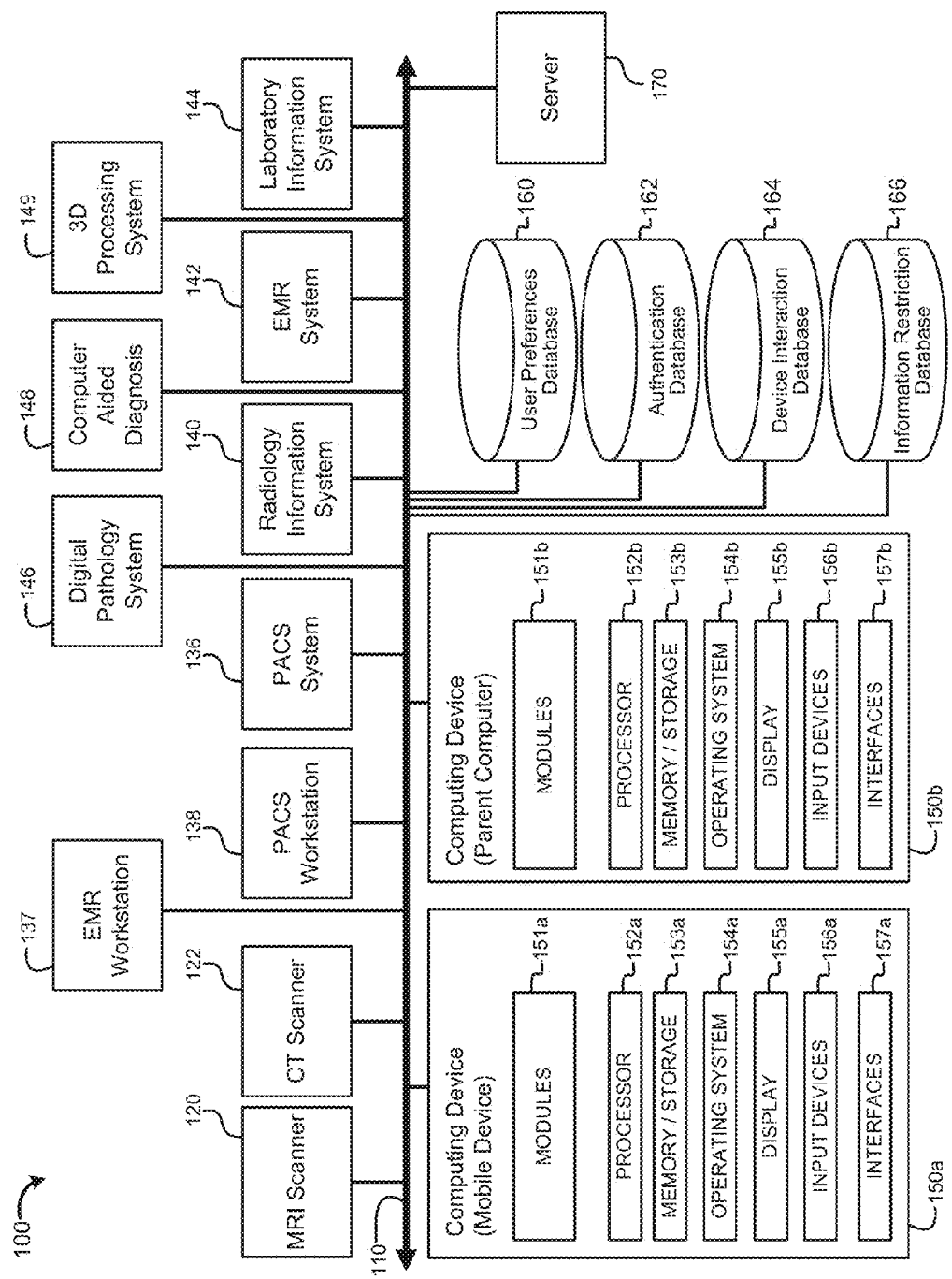
FIGS. 1A-1C are illustrative diagrams of an information restriction system in accordance with various embodiments.

Turning to FIG. 1A, an example of the computer system configured to implement the selective display of information on remote devices is provided. In the illustrated configuration, the patient data is obtained from a local network 110 of hospital subsystems 120-144, and computer devices 150a-b, each configured to input, output, store or process information concerning a patient.

In one arrangement, one or more medical scanners, such as MRI scanners 120, are connected to the network 110. As a non-limiting example, the MRI scanners 120 can be used to acquire MRI images from patients, and can share the acquired images with other devices on the network 110 by either directly storing MRI scanner images in a local storage, or uploading the images of a particular patient to that patient's data storage location in a patient database. One or more CT scanners 122 can also be coupled to the network 110. The CT scanners 122 can also be used to acquire images and, like the MRI scanner 120, can then store those images and/or share those images with other devices via the network 110. Any other scanner or device capable of inputting or generating information that can be presented to the user as images, graphics, text, or sound, including ultrasound, angiography, nuclear medicine, radiography, endoscopy, pathology, dermatology, etc. can be connected to network 110.

In another arrangement, a Picture Archiving and Communications System (PACS) 136 and/or PACS workstation 138 can be connected to the network 110. The PACS 136 is typically used for the storage, retrieval, distribution and presentation of images (such as those created and/or generated by the MRI scanner 120 and CT Scanner 122). The medical images can be stored in an independent format, an open source format, or a proprietary format. A common format for image storage in the PACS system is the Digital Imaging and Communications in Medicine (DICOM) format. The stored images may be transmitted digitally to a network accessible storage location via the PACS system, thus often reducing or eliminating the need for manually creating, filing, or transporting film jackets.

A Radiology Information System (RIS) 140 can also be connected to the network 110, as shown in the illustrated embodiment of FIG. 1A. The radiology information system 140 is typically a computerized data storage system that is used by radiology departments to store, manipulate and distribute patient radiological information such as radiology reports.

As shown, an Electronic Medical Record (EMR) system 142 and EMR workstation 137 can be connected to the network 110. The EMR system 142, when provided, is configured to store and make accessible to a plurality of medical practitioners computerized medical records. There can also be attached to the network 110 a Laboratory Information Systems 144. Laboratory Information System 144 is a system which typically is configured to store information created or generated by clinical laboratories. Likewise, a Digital Pathology System 146 can be also attached to the network and used to digitally manage and store information related to medical pathology.

Further components can be available on the network 110, such as a Computer Aided Diagnosis System (CAD) 148 and 3D Processing System 149, which can be used to analyze images and create new views of the information, e.g., 3D volumetric display, Multiplanar Reconstruction (MPR) and Maximum Intensity Projection reconstruction (MIP) respectively.

In other embodiments, other computing devices that store, provide, acquire, and/or otherwise manipulate medical data can also be coupled to the network 110 and can be in communication with one or more of the devices illustrated in FIG. 1A. For example, each of the devices described are configured to update a patient record stored in a database, such that all of the data for a given patient is accessible from a parent computing device having sufficient access privileges.

Figure 1B:
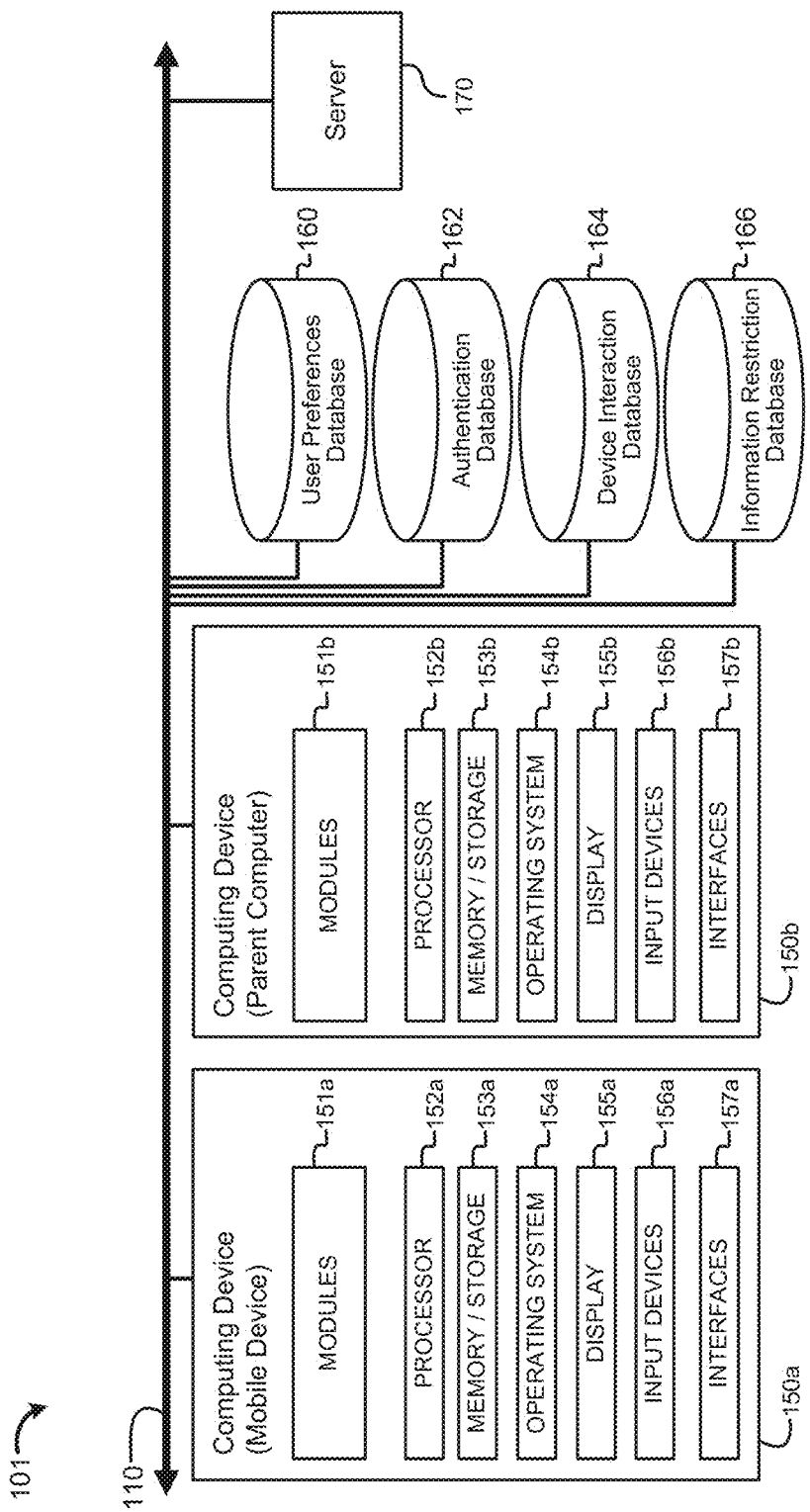

As shown in more detail in FIG. 1B, general and mobile computing devices, 150a and 150b, are connected to the network 110 and are used to access all or portions of the patient data. In one arrangement, the patient data is obtained from a file system located in the server 170. Alternatively, the computing devices are configured to access discrete pieces of information or data pertaining to a particular patient or group of patients from storage or memory locations connected directly to each of the subsystems.

In FIGS. 1a and 1b the computing device 150a is labeled as a mobile device and computing device 150b is labeled as a parent computer. However, alternative computing devices are possible and understood. In one particular configuration of the network 110, the computing devices 150a and 150b can be a computer having software or hardware modules 151-157. In other embodiments, the modules can reside on another computing device, such as a web server or other server, and the user directly interacts with a second computing device that is connected to the web server via a computer network. In one embodiment, the modules include some or all of the software utilized by the inventions described herein.

In one non-limiting example, the computing device 150a or 150b is selected from one of a variety of computing platforms such as a server, a desktop computer, a workstation, a laptop computer, a mobile computer, a Smartphone, a tablet computer, a wearable computer such as a smart watch, a wearable computer that may be interfaced to a head mounted or heads-up display, a cell phone, a personal digital assistant, a gaming system, a kiosk, an audio player, any other device that utilizes a graphical user interface, including office equipment, automobiles, airplane cockpits, household appliances, automated teller machines, self-service checkouts at stores, information and other kiosks, ticketing kiosks, vending machines, industrial equipment, and/or a television, as a non-exhaustive set of examples.

The computing devices 150a and 150b are configurable to interface with various networked devices in order to communicate, receive or update medical information that are stored centrally in a database or distributed among the various systems present in the network. It should be noted and appreciated that the computing devices 150a and 150b are general computing devices and are configurable to display any type of data commonly displayed on general computing systems.

Depending on the embodiment, the other devices illustrated in FIG. 1a (besides the computing device 150) can include some or all of the same components discussed above with reference to the computing device 150.

Figure 1C:
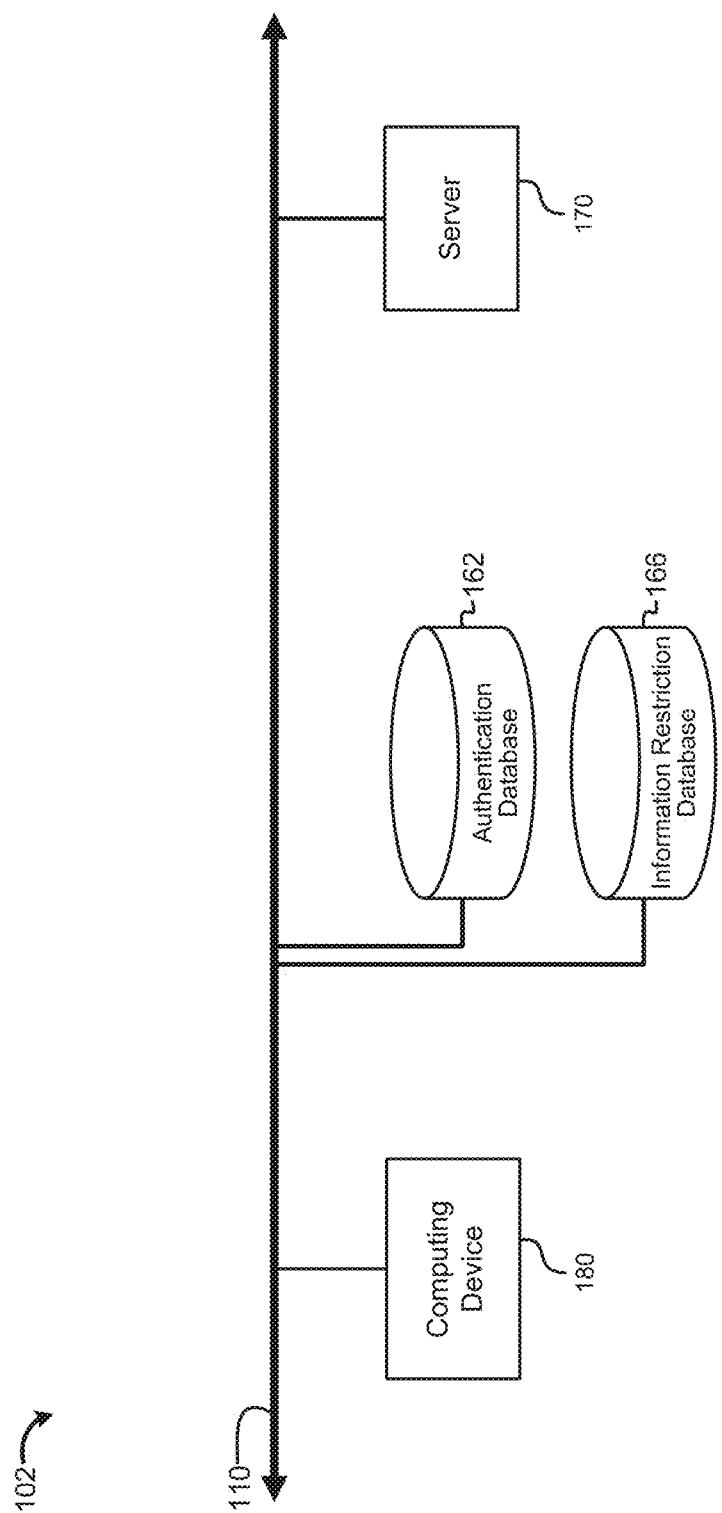

As shown in FIGS. 1A-1C, also connected to the network 110 are one or more databases 160, 162, 164, 166 that support functionality of the various computing devices connected to the network 110 and which provide a repository for instructions and algorithms related to the functioning of various embodiments of the present inventions described herein.

The databases are commonly used and understood data structures or tables that are accessible remotely, either through a server or other type of direct or remote computer configured appropriately to enable access and retention of data.

In one arrangement, the data stored in the databases are accessible to servers 170, desktop computers 150a, mobile computers 150b, or other computing devices directly connected to the network, or given access to the network 110 through a network link or portal.

The databases of the system illustrated includes a User Preferences Database 160 configured as a data storage location which contains tables and indexes that allow the computer to store and obtain data regarding a particular users/site preferences. Site preferences allow a user to set privacy levels manually depending on the display device. For example, a user can store a global access level in the user preference database that sets the privacy level for all medical test results regardless of hardware configuration. Also attached to the network is an Authentication Database 162, configured as a data storage location accessible by a processor suitably configured by code executing therein to provide user authentication services for a user. Such services include signing into, or accessing, the network from a computer such as a mobile device. Furthermore, the Authentication Database 162 contains data used to configure a processor to authenticate a new user, or an already authenticated mobile user with a different display device. The Authentication Database 162 also contains code to configure a processor to access rules governing user privileges in terms of modifying the privacy level of a device depending on the privileges associated with that user. As an example, executives or high-ranking officials have user privileges that allow for the modification of the device privacy level so as to permit the display of private information on devices not independently possessing the required privacy level.

As further provided in FIGS. 1A-B, the system includes a Device Interaction Database 164. The Device Interaction Database 164 provides storage and indexing of data related to the input and output functionality or capabilities of a display of a given type or particular device identification (e.g., a MAC address in the case of a device with an integrated display). Furthermore, the Device Interaction Database 164, in one arrangement, also stores and provides the system with the capabilities of parent computers in terms of input and output functions. Additionally, the Device Interaction Database 164 stores and provides access to data relating to how different actions and inputs (such as inputs from a mobile device or remote computer) are to be handled by the system, e.g., multitouch, accelerometer, microphone, etc., are communicated to and presented as user input to parent computers. In one arrangement, this data is presented as algorithms for evaluating and determining the access level of a device based on how the device handles inputs and outputs of the device under evaluation. Additional rules or algorithms are stored in the database regarding different outputs from parent computers, such as images, user interfaces, sound, etc., are transmitted to and presented on mobile devices.

As shown in further detail in FIG. 1C, an Information Restriction Database 166 is also connected to the network 110 and is configured to provide and store data relating to characteristics of the data stored and accessible by the network. For example, the Information Restriction Database 166 provides data detailing the privacy levels or restrictions present for a given portion of patient data. For instance, the Information Restriction Database 166 provides data in the form of rules or algorithms that instructs the remote display device, and/or a computer having access to data requests by a remote display device, to restrict access to all, or a portion of the information depending on at least the hardware configurations and/or the location for a given portion of the data set. In this regard, the rules or algorithms maintained in the database 166 can configure a processor to make a determination on the basis of the hardware configuration of the requesting device, an identification of the requesting device, or both, as to whether to provide the requested dataset or not. For instance, the requested dataset can be restricted, and therefore not provided, in the event that the hardware fails this determination.

In one example, the Information Restriction Database 166 is configured to store rules to evaluate medical exams to determine the restriction status. Likewise, other rules for data, such as patient's information, site preferences regarding restricted information and user preferences regarding restricted information are stored in the Information Restriction Database 166.

Information Restriction Database 166 contains information that configures a processor to assign a privacy level for data stored or accessible on the network. For example, data generated by each of the devices on the network, 120-144, are assigned a privacy level according to specific data handling rules stored in the Information Restriction Database 166.

The Information Restriction Database 166 also includes rules accessible by a processor in order to evaluate data sets, objects, files, folders and other collections of data and determine, based on the nature of the data, the proper restriction level for the information. For example, the system described is configured to evaluate the contents of the medical record and determine, based on the content, if the information should be restricted to a private display. These evaluations can be made in response to a data request by a user of the system. Alternatively, the records evaluated by the present system are preconfigured or coded with a general privacy level, or specific privacy level for individual data elements within the record.

In one arrangement, the Information Restriction Database 166 cooperates with a privacy classification module to configure a processor to assign a privacy level for data based on the type of information (audio, visual, etc.) as well as the information content. As an example, the privacy level classification module configures the processor to assign a given privacy level to the result of a lung biopsy according to the outcome of the test.

In one arrangement, the privacy classification module cooperates with the Information Restriction Database 166 by instructing a processor to classify or assign data at a given privacy level based on pre-set rules. In one instance, all the data is assigned a specific level of privacy at different organizational levels. For example, the data is assigned a privacy level according to a hospital or department preference, an individual doctor preference (user preference), or a user group (group preference). In one further configuration the privacy module cooperates with the Information Restriction Database 166 to assign a set privacy level to all the data associated with an individual.

Alternatively, the privacy level assignment module configures the processor to assign privacy levels for data depending on the accessing or requesting device. For example, the processor is configured, through an instruction set, to generate general or specific categories and privacy levels for restricted devices, such as Smartphones 210, Smartwatches 330, tablet computers, and Wearable computers with heads-up displays (HUD), such as the heads-up display 402, and virtual reality headsets. The system described is also configurable to evaluate the privacy level of desktop computers with heads-up displays or other small displays, where the restricted data may only be displayed on the private displays connected to these devices. The system described is also configurable to evaluate the privacy level of desktop computers with standard monitors, where the restricted data may be displayed on systems that are located in a pre-defined or user identified secure location, for example in an office where the display is only viewable by the user.

In one arrangement, the system is configurable to only allow the display of certain types of restricted information on certain types of private displays. For example, positive results of an HIV test might only be allowed to be displayed on mobile devices with screens smaller than 5".

In a further embodiment, information restriction rules contained within the Information Restriction Database 166 apply to information that a user can input. For example, prescriptions for medication might be classified as restricted information so that doctors would only be able to enter prescriptions for medications on devices with private displays.

Without loss of generality, any of the embodiments described herein can include restrictions that comprise controls which are responsive to the device connected at the end of the network path which has the display of the requesting device. The hardware connected on this path can be analyzed by code executing in a processor in order to determine the device type and/or ID of the device to which the dataset is to be transmitted. Whether transmission of the dataset is to be restricted can be assessed in view of this determination. If the device type or device ID is known to or approved by the system (e.g., based on look-ups to stored reference or authorization data), then that transmission can proceed. On the other hand, if the device type or device ID are not known or approved by the system, the system can be configured to not transmit the requested dataset in view of the hardware connected in that network path.

The system described herein can be implemented as a series of modules comprising code and executed in a processor which responds to user events, hardware connections, or both. In part, the system illustrated herein is also configured to access, retrieve, obtain and otherwise receive information that is used in support of various functionalities described herein, and can include input and output devices or be configured to communicate with such devices through network ports and drivers configured or connected for that purpose.

Turning to FIG. 7, the system or network 110 utilized in the various embodiments of the invention implements a series of steps to control the display of data on remote accessing devices based on the hardware configuration and/or location of the remote accessing device. The methods described herein are implemented utilizing the elements of the network as provided in FIG. 1. However, it should be appreciated that other additional or alternative arrangements are possible. For example, the described steps are implemented by one or more computing devices, such as the computing device 150a, but the methods are not limited to performance by the computing device 150a and should be interpreted to include performance by any one or more of the computing devices, such as additional computers or server.

The information restriction and distribution system of the present invention selectively displays information requested by a computer user based on the access level of the data and the hardware and/or location data of the computer on which the data will be reviewed. The system enables a user to review some portions of private or restricted data on standard display devices, e.g. computers, smartphones, computer tablets, interactive displays, while still ensuring that other portions that are more sensitive, are only accessible to a user on a "private display," i.e., those displays that are not easily viewed by others nearby.

With reference to FIGS. 7 and 8, the information restriction and distribution system is implemented and initiated by at least one request module 710 which comprises code executing in a processor 700 to request a specific data set, such as a medical record, from a medical record database 705 according to step 810. In the illustrated arrangement, access to the Device Interaction database 164, the Information restriction database 166 and the Medical Record Database 705 are controlled by a network controller 701, which comprises a processor configured with code executing therein.

Contemporaneous with, or subsequent to, the requesting step 810, the hardware configuration and/or location of the requesting device (i.e., the display device) is transmitted to the controlling processor as in step 820, using a hardware configuration transmitting module 720 configured as code executing in the processor 700. In one arrangement the hardware and location data are obtained by a processor configured with sub-modules to query the device operating system or hardware modules to obtain the necessary information. For instance, geolocation data, such as coordinates obtained from a GPS or equivalent receiver or transponder are used to evaluate the location of the output device. Other examples of technologies that could be used to evaluate the location of the output device include near-field communication technologies, Bluetooth and/or other low energy proximity sensing technologies. Likewise, data relating to the hardware configuration of the output device, such as audio capabilities, video display capabilities and input capabilities can be obtained from an application or operating system residing on the output device. In the alternative, the location or hardware configuration is supplied manually and transmitted according to step 820.

Once the display device has been evaluated for its location and capabilities, a privacy level is assigned to that output device and may be optionally stored in the device interaction database for future reference or transmitted in real-time to a server or database. For example, a privacy level assignment step 830 includes receiving, by the controlling processor 701, the location and configuration data transmitted by the display device processor 700 and comparing that information to preset privacy levels and rules in the Device Interaction Database and Information Restriction Database. In one arrangement this step is carried out using a privacy level assignment module 715, which operates as code executing in the controller processor 701. In one arrangement, if the privacy level of a given output device is above a minimum threshold, or pre-set limit, then the assignment module 715 configures the controller processor 701 to assign the output device a "private" level. This privacy level can, in one configuration, take the form of an entry in a table in the Information Restriction Database or the Device Interaction Database.

In an alternative embodiment, the assignment module 715 instructs the controller processor 701 to assign different portions of output components of the output device differing privacy levels depending on the hardware configuration (e.g., device type, MAC address, or other hardware-identifying information or hardware setting information), or location of the output device. For example, the controller processor 701 is instructed by the privacy level module 715 to classify on output device as a "private" device for visual data only, but as a public device for audio data, or an audio component of multi-media data.

In a further arrangement the privacy level assignment module 715 further instructs the controller processor 701 to query each output device connected to the network on a periodic basis and updates the privacy level depending on the function, location, size, and accessibility of the output device. In an alternative, the privacy level assignment module 715 includes a sub-module that configures the controller processor 701 to set privacy levels specific devices. For example, an administrator device is set to the maximum level of privacy regardless of the hardware or location data. In still a further arrangement, privacy level assignment module 715 includes a sub-module that configures the controller processor 701 to evaluate, in real-time, the privacy level of an output device depending the proximity of other individuals, general access level of data, or other factors, as can be obtained through a variety of system inputs. For example, where a output device is classified as a video "private", audio "public" device, such as a nursing station computer, the privacy level assignment module 715 configures the controller processor 701 to reclassify the output device with an audio "private" level in the event that a private audio display device (e.g. a headset, wireless or wired to the network) is connected to the output device.

It should be noted that in some cases, conventional computer monitors may be considered private displays, for example in cases where they are physically located in places were only the user of the computer can view the computer screen, such as an office. Alternatively, devices that can be classified as having private displays include smartphones, PDAs, tablets computers, interactive displays, and wearable computers, including devices with heads-up displays (HUD), such as Google Glass, virtual reality displays, such as Oculus Rift, and smartwatches, such as Apple Watch. In another example, a private display might be a computer display that is only clearly visible only to users wearing specialized glasses. In another example, a private display might be a computer display that is only clearly visible to a user who is positioned at a specific spatial position relative to the display.

In the process steps of FIG. 8, once the privacy level of the output device has been determined, it is compared to the privacy level of the data requested from the medical record database as in step 840. In one arrangement, a comparison module 725, configured as code executing in the controller processor 701, instructs the processor to evaluate the privacy level of the data requested and determine if the requesting output device has a sufficient privacy level to allow the display of the requested data.

In the event that the requesting device has a sufficient privacy level compared to the requested information, the some or all of the requested data is transmitted from the medical database to the output device, as in step 850. In a particular embodiment, a data transmission module 735, configured as code executing in the controller processor 701 instructs the processor to transmit those portions of the requested data to the display device.

Furthermore, the system described is configured to segment, or access segmented private information such that portions of the private information are distributed across multiple devices depending on the privacy level of the device and the privacy level of the information.

Once the data has been received by the display device, it is displayed or output by the display device, according to step 860. In a particular embodiment, a display module 730 configured as code executing in the display device processor 700 instructions the processor to display the permitted data received from the medical record database.

In the event that a hardware configuration or location changes in the output device, such as the connection of an external headset, a real-time device evaluation module 740 configures the display device processor to communicate the updated status of the display device to the controller processor 701. This, in turn, causes the controller processor 701 to update the privacy level of the output device and cause additional, newly available data to be sent to the output device for display.

Figure 2:
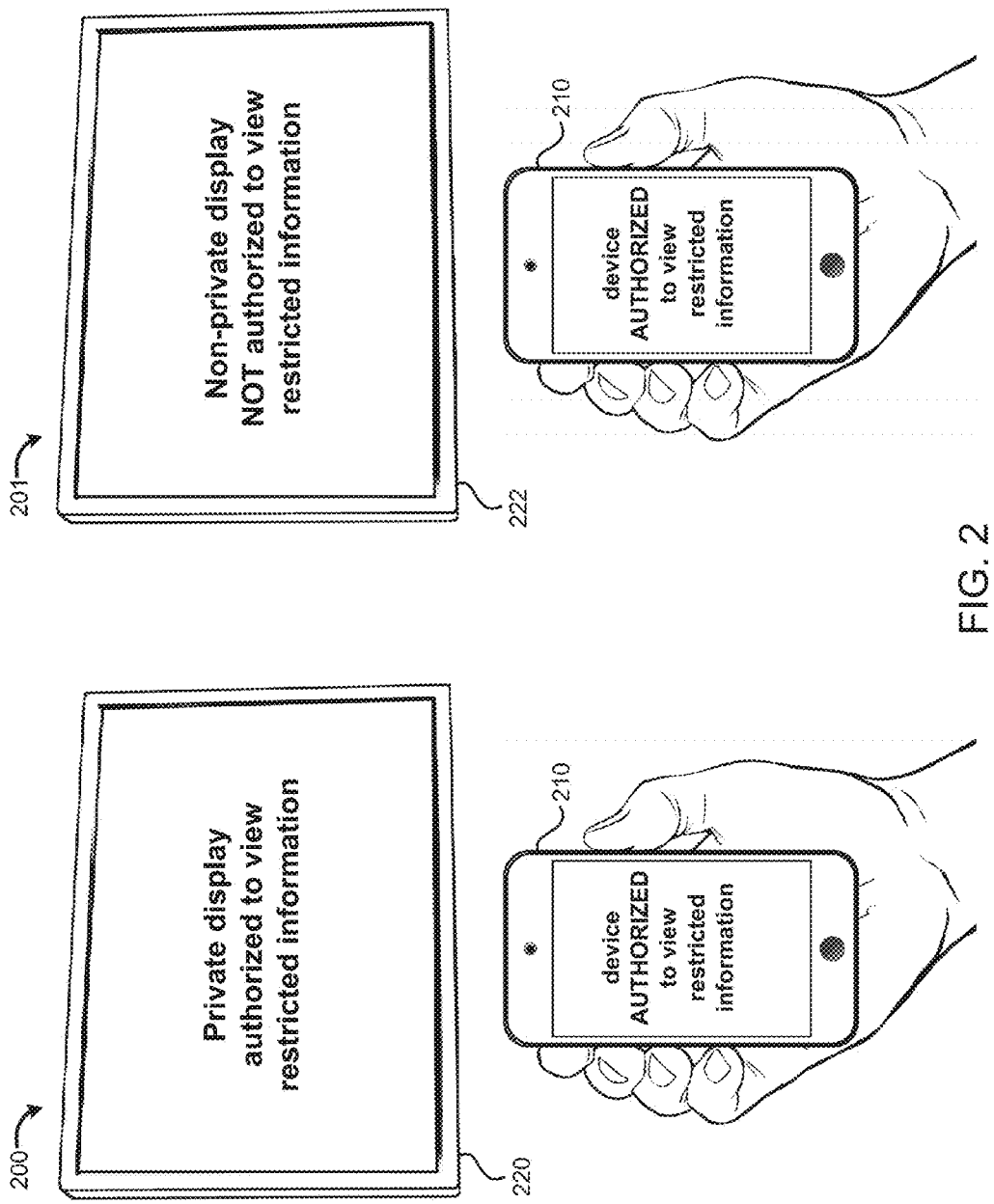
FIG. 2 is a diagram of a mobile device and a private and non-private (public) display as can be used in the information restriction system such as shown in FIGS. 1A-1C.

Returning to FIG. 2, once a display device has been assigned a privacy level, data accessed by that output device will be conditioned based on the privacy level of the device as a whole, or the individual components of the output device. Requesting data from a device having an insufficient privacy level will result in a placeholder data being sent to the output device indicating that the data is not accessible from the given device. As illustrated, the display configuration 200 includes computer display 220, and a mobile device 210. In the illustrated configuration, both the computer and the mobile device are classified as private devices. As such, when data is requested, it can be displayed on either of the requesting devices.

Alternatively, the display configuration 201 includes a computer display 222 and the same mobile device 201. In this configuration, the computer display 222 is not classified as a private device, while the mobile device 201 is classified as a private device for displaying the data requested. In one configuration, a placeholder note or statement indicating the user is not able to access the requested data using that particular device is supplied to the screen. In a further arrangement, the placeholder data indicates the necessary level of privacy needed for the data to be viewed on that device.

In a further example, the mobile device 210 and the restricted computer 222 are used together to allow the user to view medical information on a same patient. However, in this configuration restricted information is only displayed on output device 210. Similarly, restricted information in the form of audio would only be playable on device 210, which is classified as a "private display" as it related to audio information.

Figure 3:
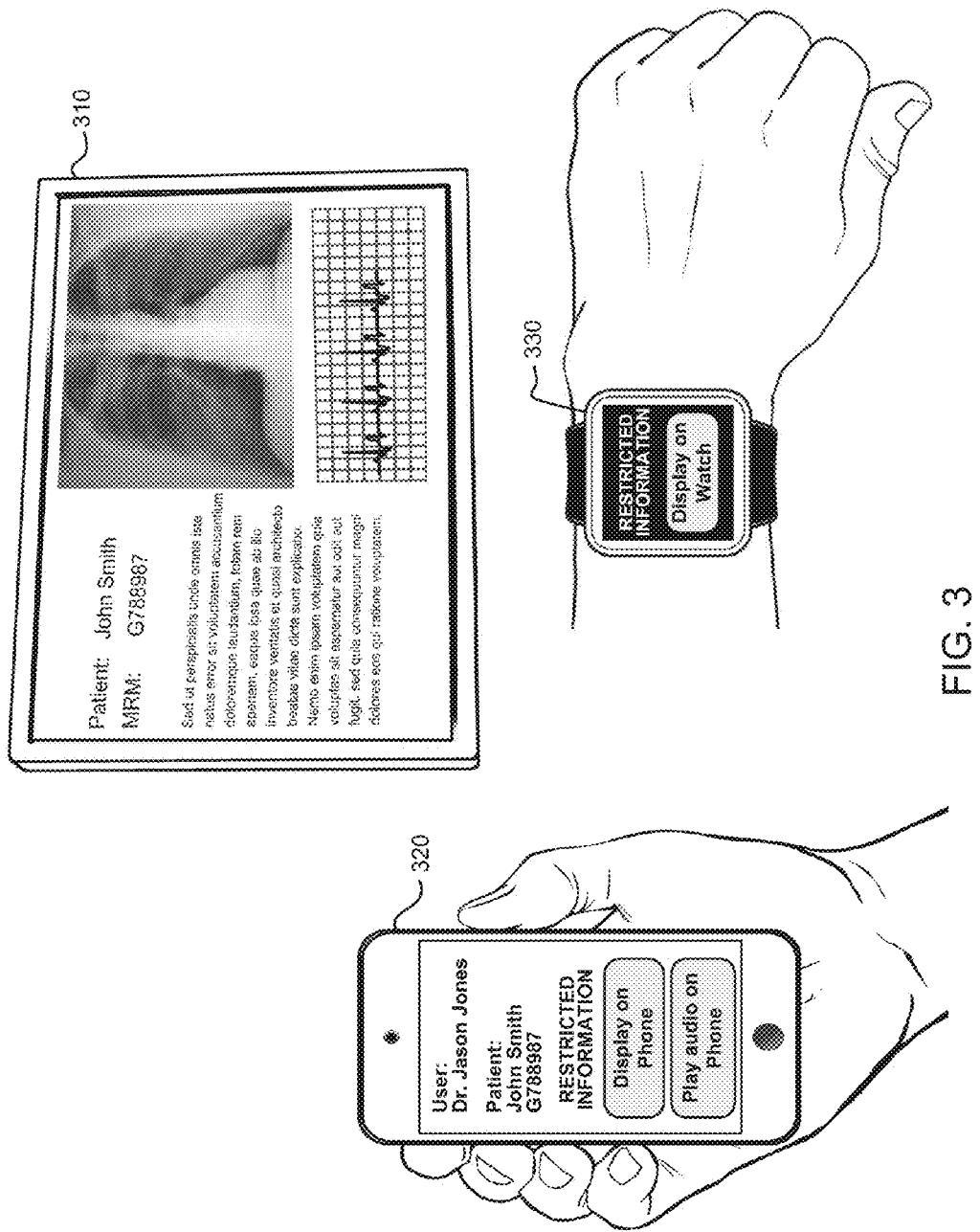
FIG. 3 is an example of private and non-private displays according to one embodiment of the described system.

In one particular configuration as illustrated in FIG. 3, a large, publically viewable display 310, as well as a mobile device 320, and wearable device 330 are incorporated into the system described. The computer display 310, because of its large size and location, is classifiable as a "non-private" display, and is prohibited from displaying private level information. Alternatively, the mobile device 320 is classified according to the system as a "private display." In a circumstance where the data requested by the mobile device includes an audio and visual component, the data returned by the system will include only visual data, but not audio data. This is due to the privacy level assessment module 715 as described in FIG. 7, instructing the processor to determine that the audio configuration of the mobile device did not permit the output of audio information. Thus, the privacy level assignment module 715 configures the controller processor 701 to classify the output device 320 as a private device for visual data, but as a public device for audio data.

In the example shown, device 320 and the computer associated with display 310 are both accessing information on the same patient. Here, the user is authorized to view information on a particular patient. Since device 320 has a private display, the user can access restricted visual information. In the event that the user connected a private audio peripheral device to device 320, then restricted audio information is also accessible by the user. Furthermore, additional or alternative information is available to the smartwatch 330 based on the audio and display configurations available to the user.

Figure 4:
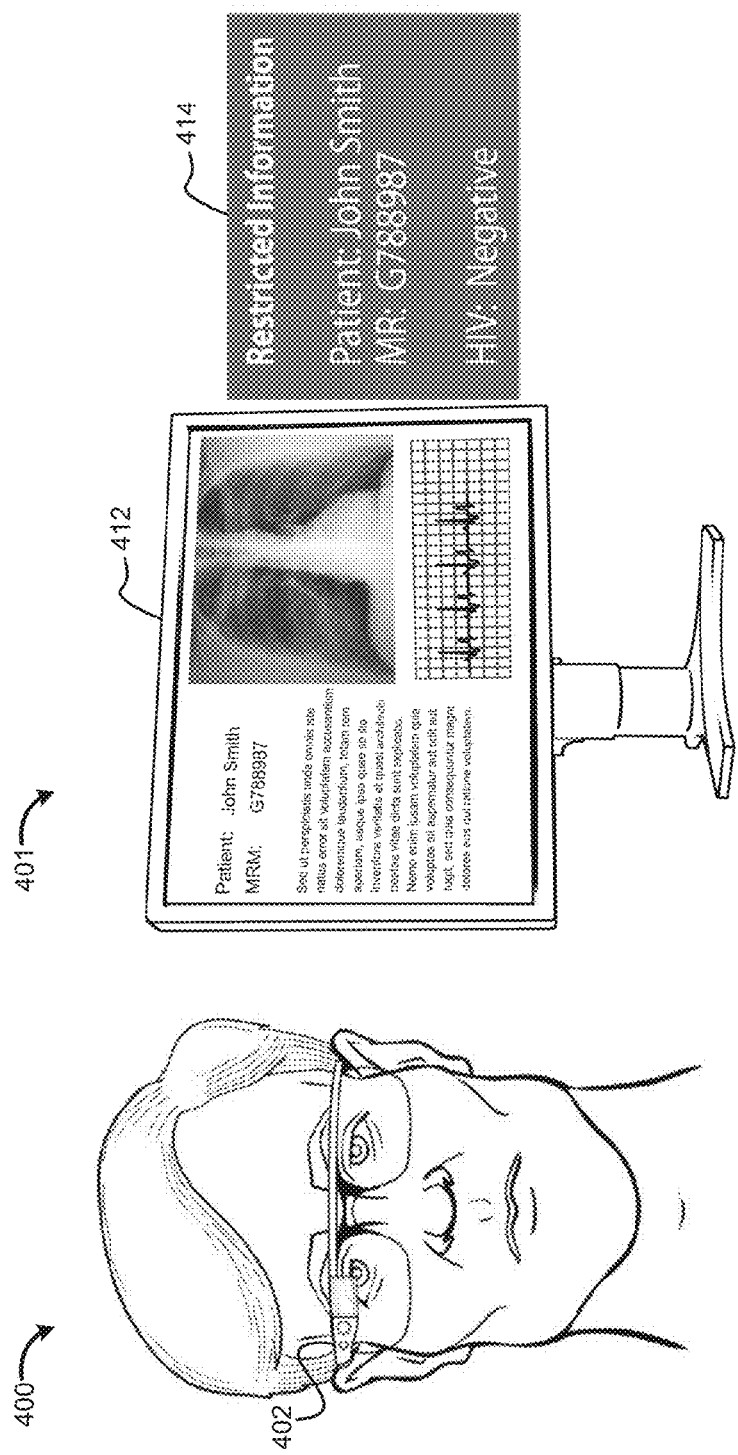
FIG. 4 is an example of a display device configured in accordance with an embodiment of the described system.

As shown in FIG. 4, the display configuration 400 provides an example of a heads-up display (HUD) 402 connected to a conventional computer, such as a desktop or laptop computer, or that can be part of a wearable computer.

View 401 is an example of the visual field observable while wearing a HUD such as example HUD 402. In the example shown the user is viewing information related to a patient that is being displayed on a computer monitor and being displayed on the HUD. In the example, region 414 is information in the user's visual field being presented by the HUD. In the example shown, the HUD is classified as a private display and therefore the user is able to view restricted information via the HUD (example region 414) that is not displayed on the computer display 412, which is a non-private display.

Other head mounted display systems could also be classified as private displays, including those in which the display of the system is the only thing the user can see while wearing them, such as a virtual reality display system.

Figure 5:
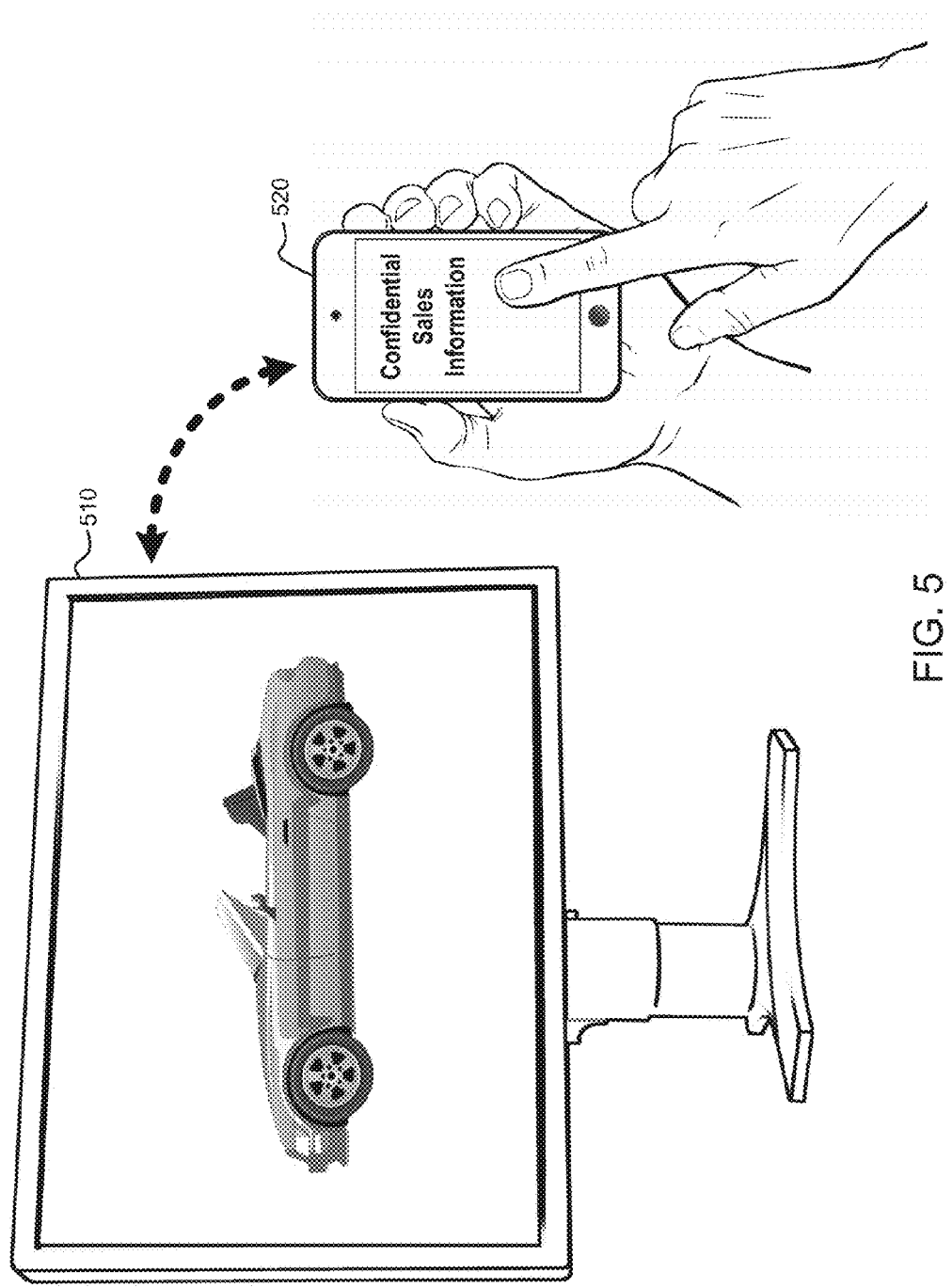
FIG. 5 is an alternative example of a display device configured in accordance with an embodiment of the described system.

Turning to a non-medical example of information restriction, FIG. 5 illustrates the use of the system in a retail environment. Computer display 510 is evaluated by the restrictive data display system and determined to be a public display, thus only displaying information related to a specific good or service (e.g., cars) for sale. In this configuration, the controller processor of FIG. 7 restricts portions of the data requested from the database depending on the privacy level of the display. As shown, the public display only provides general information concerning the item for sale. However, through the implementation of the steps and modules provided herein, a user of a private display configuration device is able to access pricing information or other data.

FIGS. 6A-6D illustrate flow charts detailing specific implementations and embodiments of the system and method for restricting information based on output device characteristics.

Figure 6A:
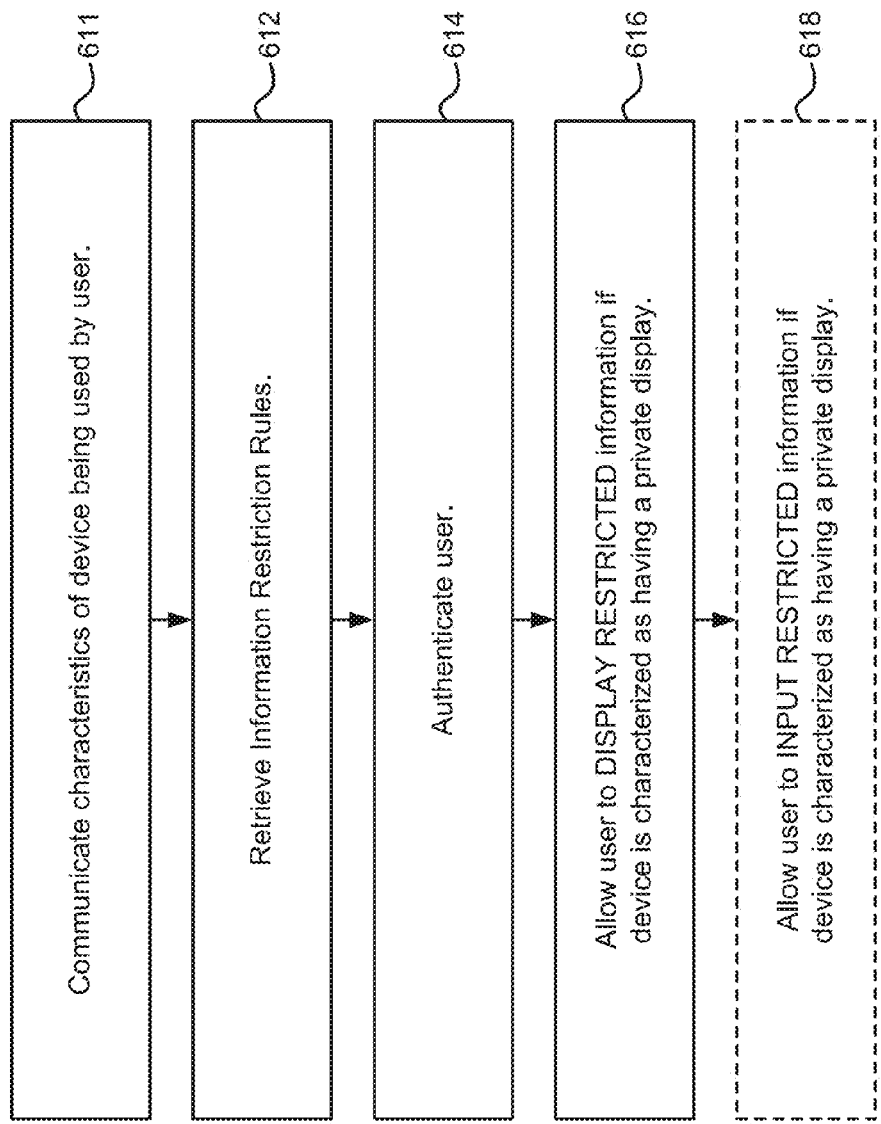

FIG. 6A is a flow chart illustrating steps related to systems and methods that manage the display and/or input of restricted information on devices with private vs. non-private displays. In a step 611 the user attempts to access data located or routed by the server 170. As a response, the characteristics of the requesting device are transmitted to the server 170. As shown in step 612, information rules are retrieved from Information Restriction Database 166 and the device characteristics are evaluated against the restriction rules in the database 166. For example, the device characteristics and information restriction rules are also utilized in the authentication process such that the user only is authenticated when he is using a device with a private display. For example, an EMR can be configured with Information Restriction Rules that prevent any access with devices that do not have private displays.

The server 170, in one configuration, authenticates the user by requesting credentials (e.g., username, password, fingerprint, etc.) as shown in step 614. In another embodiment, steps 612 and 614 are reversed, so that user authentication occurs before information restriction rules are retrieved.

As provided in Step 616, the user utilizes computing device 180 to access information communicated by server 170, server 170 utilizes Information Restriction Rules stored in Information Restriction Database 166 to determine which information is restricted and will only communicate restricted information to devices characterized as having private displays.

In an additional step 618, the system is configured to allow the input or transmission of private information, if that information is being entered on a device having a private display. The input or "display" of information could apply to visually displayed information, e.g., images, text, graphs, etc., as well as audio information.

FIG. 6B provides an example of a flow diagram of the implementation of the authentication step 614, for example, by a series of modules configured as code executing in a processor. As shown in step 612, the requesting device hardware configuration is provided to the server 170, using a transmitting module 720 as provided in FIG. 7. In turn the server 170 implements an evaluation step 622 to determine if the hardware configuration meets the requirements for a private display. In one arrangement this is implemented using the module 715. In this particular configuration, if the display device does not have a private display, then the data is not accessed and provided to the mobile device. Alternatively, if the requesting device is equipped with a private display, then the server 170 requests authentication data as in step 624.

In the event that the log-in credentials are verified, according to a verification step 625, the user is authenticated, as in step 627. In one configuration, the authentication is accomplished as a series of modules configured as code executing in the processor of the server and configured to instruct the processor to access the user database, compare the user credentials to a stored table of users and to confirm authentication of a user.

Once the user is authenticated and the device characteristics have been evaluated by the system according to steps 631-633 of FIG. 6c, the data requested is either transmitted to the display device or a placeholder statement is transmitted to the display device, according to the privacy level of the device, the user credentials and the privacy level of the information requested, as in step 635.

Figure 6D:
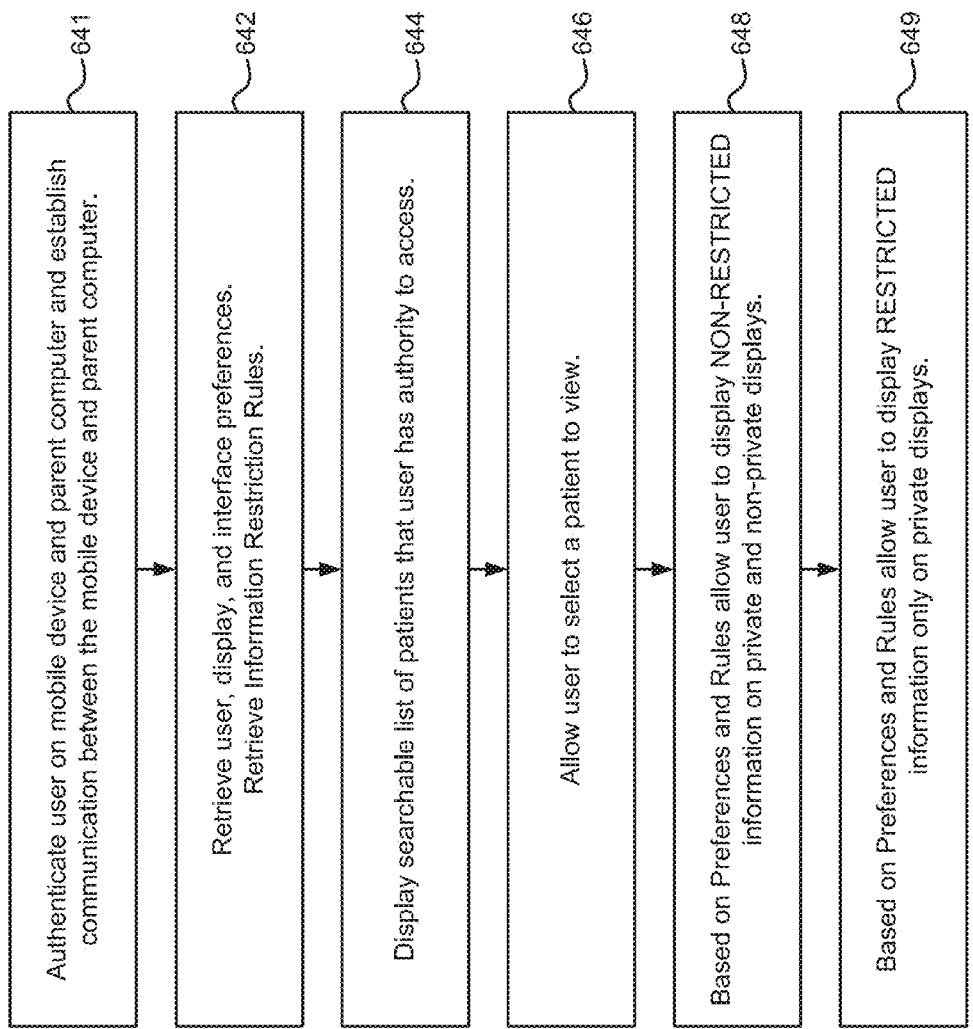

FIG. 6D provides an alternative flow diagram of the operation of the system of restricting access to data based on the privacy level of the device. As shown, the user is authenticated by the server as in step 641 and transmits the device configuration to the server. The server also retrieves the user preferences, the device configuration and the interface preferences as well as retrieving Information Restriction rules from the information restriction rules database 166 as in step 642.

Once the rules are retrieved, the authenticated user is permitted by a processor suitably configured by code, to access a list of datasets, such as a patient list, that the authenticated user is permitted to access, as in step 644. Once the user causes the selection of a particular data set, the processor is configured by code to transmit only data that meets the privacy level on the device as in step 648. In step 649, the processor of the user device is configured by code to display the selected information received.

FIG. 9 provides examples of various display devices (910, 912, 914, 916) having differing restriction levels. FIG. 9 also provides examples of the relative privacy levels and information privacy rules attached to each device according to a database or look-up table. Table 920 is an example of the Device Privacy Levels assigned to various devices based on the hardware configuration and/or location. The higher privacy levels are assigned to devices that are more secure in terms of their ability to prevent people other than the user from viewing and/or hearing information presented by the device. While the example shows six privacy levels, labeled 0 to 5, in practice any number of privacy levels greater than one can be utilized.

In a particular arrangement, the device privacy levels may also vary depending on the device user. In one arrangement, the access level for a particular device can change in response to specific or authenticated user that is currently using the device. For example, a device that is authenticated using a login/password, fingerprint scanner, or other biometric based access device has a privacy level that reflects the privacy level assigned to that user regardless of the hardware configuration.

The Device Privacy Levels may be set as a user, group and/or site preference, and may be stored, for example, in the Device Interaction Database 164 or Information Restriction Database 166.

In the example of the Device Privacy Levels shown, the Privacy Level assigned to computer monitor 910 is dependent on its location, i.e., the privacy level is set to 4 if located in a private doctor's office, 2 if located in a nursing station, 0 if located in another location or if its location is unknown. In one arrangement, devices with unknown locations are assigned a privacy level based on the hardware configuration of the device. In the alternative, the system described assigns devices having an unknown location to a pre-set privacy level.

In one particular arrangement, smartphone 912 is assigned a Privacy Level 4 when it is located in the hospital. The location of the smartphone 912 is determined in one instance by GPS transponders or another technology capable of locating its position. In this particular configuration, when the smartphone is no longer located within the hospital, the device is assigned a Privacy Level of 3. Alternatively, the smartwatch 914 is assigned a privacy level of 4, regardless of its location. Likewise, heads-up display 916 would be assigned a Privacy Level of 5, regardless of its location.

Table 930 illustrates example Information Privacy Rules that determine whether information can be presented on a device based on the Device Privacy Level of a given device. Information Restriction Rules may be set as a user, group and/or site preference, and may be stored, for example, in Information Restriction Database 166. In one embodiment, information will be displayed on a device when the Privacy Level of the Device is greater than or equal to the Privacy Level of the Information. For example, the results of a Fetal Ultrasound are assigned an Information Privacy Level of 3 in the example shown. Therefore, the results of the Fetal Ultrasound would be displayed on any device with a Device Privacy Level of 3 or greater.

Information Privacy Rules, in one arrangement, assigns an Information Privacy Level to virtually any type of information. For example, various types of information about a patient may be assigned different privacy levels. As illustrated, a patient's gender, which is generally apparent based on the patient's name and appearance, may be assigned a low Privacy Level, such as 0. Alternatively, the patient's date of birth may be assigned a higher Privacy Level, such as 1, as illustrated in Table 930.

It should be appreciated that whether or not a particular test or exam has been ordered or performed on a patient may reveal private information about the patient, and therefore that information may also be assigned a Privacy Level. For example, the fact that a Fetal Ultrasound has been ordered or performed on a patient indicates that the patient was pregnant at that time of the test. Thus, the ordering of certain tests (e.g., Fetal Ultrasound) is assigned a Privacy Level of 2. Therefore, an Electronic Medical Records (EMR) or other medical record systems that contain a record of tests requested or performed are also subject to Device Privacy Levels. In the example shown, the results of the Fetal Ultrasound, which can include information such as images, audio information, measurements, a report, etc., are assigned an Information Privacy Level of 3.

Information Privacy Rules may be stored, for example, in Information Restriction Database 166. Information Privacy Rules may vary based on user, group, and site preferences.

In addition, Information Privacy Rules may vary based on characteristics of the patient and/or may be determined automatically based on characteristics of the patient. For example, Information Privacy Rules might differ for pregnant vs. non-pregnant women, minors vs. adults, and patient's with a particular diagnosis vs. those without that diagnosis. In addition, Information Restriction Rules could be set explicitly for a particular patient. In one configuration, the Information Restriction Rules are configured based on instructions or rules set by the patient or the patient's physician or care giver. In the alternative, a patient who is a notorious or public figure could implement Information Privacy Rules with elevated Information Privacy Levels based on instructions by the patient or an administrator of the hospital caring for the patient.

Depending on the embodiment, the methods described with reference to the flowcharts, as well as any other methods discussed herein, can include fewer or additional blocks and/or the blocks can be performed in a different order than is illustrated. As illustrated in FIG. 10, the server and other computers of the described system can be implemented according to the computing system 1300 illustrated in FIG. 10. As shown, the computer system 1300 includes a processor 1302, a memory 1304, a storage device 1306, a high-speed interface 1308 connecting to the memory 1304 and multiple high-speed expansion ports 1310, and a low-speed interface 1312 connecting to a low-speed expansion port 1314 and the storage device 1306. Each of the processor 1302, the memory 1304, the storage device 1306, the high-speed interface 1308, the high-speed expansion ports 1310, and the low-speed interface 1312, are interconnected using various buses, and can be mounted on a common motherboard as shown in FIG. 9, or in other manners as appropriate. The processor 1302 can process instructions for execution within the computing device 1300, including instructions stored in the memory 1304 or on the storage device 1306 to display graphical information for a GUI on an external input/output device, such as a display 1316 coupled to the high-speed interface 1308. In other embodiments, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

A mobile computing device 1350 may include a processor 1352, a memory 1364, and an input/output device such as a display 1354, a communication interface 1366, and a transceiver 1368, among other components. The mobile computing device 1350 can also be provided with a storage device, such as a micro-drive or other device, to provide additional storage. Each of the processor 1352, the memory 1364, the display 1354, the communication interface 1366, and the transceiver 1368, are interconnected using various buses, and several of the components can be mounted on a common motherboard or in other manners as appropriate.

The processor 1352 can communicate with a user through a control interface 1358 and a display interface 1356 coupled to the display 1354. The display 1354 can be, for example, a TFT (Thin-Film-Transistor Liquid Crystal Display) display or an OLED (Organic Light Emitting Diode) display, or other appropriate display technology. The display interface 1356 can comprise appropriate circuitry for driving the display 1354 to present graphical and other information to a user. The control interface 1358 can receive commands from a user and convert them for submission to the processor 1352. In addition, an external interface 1362 can provide communication with the processor 1352, so as to enable near area communication of the mobile computing device 1350 with other devices. The external interface 1362 can provide, for example, for wired communication in some embodiments, or for wireless communication in other embodiments, and multiple interfaces can also be used.

The memory 1364 stores information within the mobile computing device 1350. The memory 1364 can be implemented as one or more of a computer-readable medium or media, a volatile memory unit or units, or a non-volatile memory unit or units. An expansion memory 1374 can also be provided and connected to the mobile computing device 1350 through an expansion interface 1372, which can include, for example, a SIMM (Single In Line Memory Module) card interface. The expansion memory 1374 can provide extra storage space for the mobile computing device 1350, or can also store applications or other information for the mobile computing device 1350. Specifically, the expansion memory 1374 can include instructions to carry out or supplement the processes described above, and can include secure information also. Thus, for example, the expansion memory 1374 can be provided as a security module for the mobile computing device 1350, and can be programmed with instructions that permit secure use of the mobile computing device 1350. In addition, secure applications can be provided via the SIMM cards, along with additional information, such as placing identifying information on the SIMM card in a non-hackable manner.

The mobile computing device 1350 can communicate wirelessly through the communication interface 1366, which can include digital signal processing circuitry where necessary. The communication interface 1366 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 1368 using a radio-frequency. In addition, short-range communication can occur, such as using a Bluetooth, WiFi, or other such transceiver (not shown). In addition, a GPS (Global Positioning System) receiver module 1370 can provide additional navigation- and location-related wireless data to the mobile computing device 1350, which can be used as appropriate by applications running on the mobile computing device 1350.

The mobile computing device 1350 can also communicate audibly using an audio codec 1360, which can receive spoken information from a user and convert it to usable digital information. The audio codec 1360 can likewise generate audible sound for a user, such as through a speaker, e.g., in a handset of the mobile computing device 1350. Such sound can include sound from voice telephone calls, recorded sound (e.g., voice messages, music files, etc.) and sound generated by applications operating on the mobile computing device 1350.

The mobile computing device 1350 can be implemented in a number of different forms, as shown in FIG. 10. For example, it can be implemented as a cellular telephone 1380. It can also be implemented as part of a smart-phone 1382, personal digital assistant, or other similar mobile device.

Various embodiments of the systems and techniques described here can be realized in digital electronic circuitry, integrated circuitry, specially designed ASICs (application specific integrated circuits), computer hardware, firmware, software, and/or combinations thereof. These various embodiments can include embodiment in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable storage medium and computer-readable storage medium refer to any non-transitory computer program product, apparatus and/or device (e.g., magnetic discs, optical disks, memory, Programmable Logic Devices (PLDs)) used to provide machine instructions and/or data to a programmable processor, including a machine-readable storage medium that receives machine instructions as a machine-readable signal. The term machine-readable signal refers to any signal used to provide machine instructions and/or data to a programmable processor. A non-transitory machine-readable storage medium does not include a transitory machine-readable signal.

To provide for interaction with a user, the systems and techniques described here can be implemented on a computer having a display device (e.g., a CRT (cathode ray tube) or LCD (liquid crystal display) monitor) for displaying information to the user and one or more input devices, such as a keyboard, pointing device (e.g., a mouse or a trackball), touch screen, or microphone, by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server 1324), or that includes a middleware component (e.g., an application server 1320), or that includes a front end component (e.g., a client computer 1322 having a graphical user interface or a Web browser through which a user can interact with an embodiment of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific embodiment details, these should not be construed as limitations on the scope of any embodiment or of what can be claimed, but rather as descriptions of features that can be specific to particular embodiments of particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain embodiments, multitasking and parallel processing can be advantageous.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the Restricted Display systems and methods is not intended to be exhaustive or to limit the systems and methods described to the precise form disclosed. While specific embodiments of, and examples for, the Restricted Display device systems and methods are described herein for illustrative purposes, various equivalent modifications are possible within the scope of other Restricted Display systems and methods, as those skilled in the relevant art will recognize. The teachings of the Restricted Display systems and methods provided herein can be applied to other processing and measurement systems and methods, not only for the systems and methods described above. While medical and commercial applications were used as examples, the systems and methods described herein can be applied to any field where it may be desirable to restrict display of private or sensitive information, such as military, financial, legal, insurance, and law enforcement applications.

The elements and acts of the various embodiments described above can be combined to provide further embodiments. These and other changes can be made to the Restricted Display systems and methods in light of the above detailed description.

In general, in the following claims, the terms used should not be construed to limit the Restricted Display systems and methods to the specific embodiments disclosed in the specification and the claims, but should be construed to include all systems and methods that operate under the claims. Accordingly, the Restricted Display systems and methods are not limited by the disclosure, but instead the scope of the Restricted Display systems and methods is to be determined entirely by the claims.

It should be understood that various combinations, alternatives and modifications of the present invention could be devised by those skilled in the art in view of this disclosure. The present invention is intended to embrace all such alternatives, modifications and variances that fall within the scope of the appended claims. While the invention has been particularly shown and described with reference to a preferred embodiment thereof, it will be understood by those skilled in the art that various changes in form and details may be made therein without departing from the spirit and scope of the invention.

What is claimed is:

1. A computer-implemented method comprising:
   by one or more processors executing program instructions:
   determining based at least in part on patient medical information in a dataset, an access restriction level of the dataset;
   receiving, from a display device, a request for the dataset, wherein the dataset comprises an audio feature and a visual feature;
   accessing data indicative of one or more physical characteristics of the display device;
   determining, based at least in part on the physical characteristics of the display device, an access restriction level of the display device;
   comparing the access restriction level of the display device and the access restriction level of the dataset;
   in response to the comparison, communicating or not communicating at least the visual feature of the dataset to the display device;
   monitoring an audio configuration of the display device; and
   in response to determining that the audio configuration of the display device indicates that the display device is not configured to output the audio feature through a private audio device, not communicating the audio feature to the display device.

2. The computer-implemented method of claim 1, wherein the dataset is communicated to the display device in response to the comparison indicating that the access restriction level of the display device satisfies the access restriction level of the dataset, the method further comprising:
   by one or more processors executing program instructions:
   causing the display device to display the visual feature of the dataset.

3. The computer-implemented method of claim 1, wherein the visual feature of the dataset is not communicated to the display device in response to the comparison indicating that the access restriction level of the display device does not satisfy the access restriction level of the dataset.

4. The computer-implemented method of claim 3 further comprising:
   by one or more processors executing program instructions:
   accessing data indicative of one or more physical characteristics of a second display device;
   determining, based at least in part on the physical characteristics of the second display device, an access restriction level of the second display device;
   comparing the access restriction level of the second display device and the access restriction level of the dataset; and
   in response to the comparison, communicating at least the visual feature of the dataset to the second display device.

5. The computer-implemented method of claim 1 further comprising:
   by one or more processors executing program instructions:
   monitoring the hardware configuration of the display device; and
   dynamically updating the access restriction level of the display device in response to a change in the hardware configuration that causes a change in the one or more physical characteristics of the display device.

6. The computer-implemented method of claim 1, further comprising:
   by one or more processors executing program instructions:
   authenticating a user of the display device; and
   updating the access restriction level of the display device in response to authenticating the user.

7. The computer-implemented method of claim 1, wherein determining the access restriction level of the display device comprises:
    by one or more processors executing program instructions:
        determining the access restriction level of the display device based at least in part on a display screen size of the display device.

8. The computer-implemented method of claim 1, wherein determining the access restriction level of the display device further comprises:
    by one or more processors executing program instructions:
        determining the access restriction level of the display device based at least in part on a location of the display device.

9. The computer-implemented method of claim 1, wherein the computer-implemented method further comprises:
    by one or more processors executing program instructions:
        detecting that the audio configuration of the display device has changed to output audio through a private audio device; and
        in response to detecting that the audio configuration of the display device has changed such that the display device is configured to output the audio feature through a private audio device, communicating the audio feature to the display device.

10. The computer-implemented method of claim 1, wherein the dataset comprises a first visual feature and a second visual feature, wherein the first visual feature has a different access restriction level from the second visual feature.

11. The computer-implemented method of claim 10, wherein the communicating further comprises:
    by one or more processors executing program instructions:
        transmitting, to the display device, only features of the dataset which have an access restriction level that satisfy the access restriction level of the display device.

12. The computer-implemented method of claim 10, further comprising:
    by one or more processors executing program instructions:
        transmitting the first visual feature to a first display device having first access restriction level; and
        transmitting the second visual feature to a second display device having a second access restriction level.

13. The computer-implemented method of claim 1, further comprising:
    by one or more processors executing program instructions:
        receiving input data from the display device when the access restriction level of the display device satisfies a threshold; and
        updating the dataset to include the input data.

14. A system comprising:
    a non-transitory computer readable storage medium having program instructions embodied therewith; and
    one or more processors configured to execute the program instructions to cause the one or more processors to:
        determine, based at least in part on patient medical information in a dataset, an access restriction level of the dataset, wherein the dataset comprises an audio feature and a visual feature;
        receive, from a display device, a request for the dataset;
        access data indicative of one or more physical characteristics of the display device;
        determine, based at least in part on the physical characteristics of the display device, an access restriction level of the display device;
        compare the access restriction level of the display device and the access restriction level of the dataset;
        in response to the comparison, communicating or not communicating at least the visual feature of the dataset to the display device;
        monitoring an audio configuration of the display device; and
        in response to determining that the audio configuration of the display device indicates that the display device is configured to output the audio feature through a private audio device, communicating the audio feature to the display device.

15. The system of claim 14, wherein the visual feature of the dataset is not communicated to the display device in response to the comparison indicating that the access restriction level of the display device does not satisfy the access restriction level of the dataset.

16. The system of claim 15, wherein the one or more processors are configured to execute the program instructions to further cause the one or more processors to:
    access data indicative of one or more physical characteristics of a second display device;
    determine, based at least in part on the physical characteristics of the second display device, an access restriction level of the second display device;
    compare the access restriction level of the second display device and the access restriction level of the dataset; and
    in response to the comparison, communicate the visual feature of the dataset to the second display device.

17. The system of claim 14, wherein determining the access restriction level of the display device comprises:
    determining the access restriction level of the display device based at least in part on a display screen size of the display device.

18. The system of claim 14, wherein determining the access restriction level of the display device further comprises:
    determining the access restriction level of the display device based at least in part on a location of the display device.

19. A computer program product comprising a non-transitory computer readable storage medium having program instructions embodied therewith, the program instructions executable by one or more processors to cause the one or more processors to:
    determine, based at least in part on patient medical information in a dataset, an access restriction level of the dataset, wherein the dataset comprises an audio feature and a visual feature;
    receive, from a display device, a request for the dataset;
    access data indicative of one or more physical characteristics of the display device;
    determine, based at least in part on the physical characteristics of the display device, an access restriction level of the display device;
    compare the access restriction level of the display device and the access restriction level of the dataset;

in response to the comparison, communicating or not communicating at least the visual feature of the dataset to the display device;

monitoring an audio configuration of the display device; and in response to determining whether or not the audio configuration of the display device indicates that the display device is configured to output the audio feature through a private audio device, communicating or not communicating the audio feature to the display device.

20. The computer program product of claim 19, wherein the visual feature of the dataset is not communicated to the display device in response to the comparison indicating that the access restriction level of the display device does not satisfy the access restriction level of the dataset, and wherein the program instructions are executable by one or more processors to further cause the one or more processors to:

access data indicative of one or more physical characteristics of a second display device;

determine, based at least in part on the physical characteristics of the second display device, an access restriction level of the second display device;

compare the access restriction level of the second display device and the access restriction level of the dataset; and in response to the comparison, communicate at least the visual feature of the dataset to the second display device.

\* \* \* \* \*